US009579367B2

(12) United States Patent
Pryzdial

(10) Patent No.: US 9,579,367 B2
(45) Date of Patent: Feb. 28, 2017

(54) C-TERMINALLY TETHERED AMINO ACIDS AND THEIR FIBRINOLYTIC THERAPEUTIC USES

(71) Applicant: CANADIAN BLOOD SERVICES, Ottawa (CA)

(72) Inventor: Ed Pryzdial, Vancouver (CA)

(73) Assignee: Canadian Blood Services, Ottawa (CA)

( * ) Notice: Subject to any disclaimer, the term of this patent is extended or adjusted under 35 U.S.C. 154(b) by 153 days.

(21) Appl. No.: 14/303,101

(22) Filed: Jun. 12, 2014

(65) Prior Publication Data

US 2014/0369992 A1    Dec. 18, 2014

Related U.S. Application Data

(60) Provisional application No. 61/834,613, filed on Jun. 13, 2013.

(51) Int. Cl.

| | | |
|---|---|---|
| *A61K 38/36* | (2006.01) | |
| *A61K 38/48* | (2006.01) | |
| *C07D 207/452* | (2006.01) | |
| *C12N 9/74* | (2006.01) | |
| *C12N 9/48* | (2006.01) | |
| *A61K 38/49* | (2006.01) | |
| *C12N 9/64* | (2006.01) | |

(52) U.S. Cl.
CPC .......... *A61K 38/4846* (2013.01); *A61K 38/49* (2013.01); *C07D 207/452* (2013.01); *C12N 9/6432* (2013.01); *C12Y 304/21006* (2013.01)

(58) Field of Classification Search
CPC ................ A61K 38/4846; A61K 38/49; A61K 38/4833; C07D 207/452; C12N 9/6432; C12N 9/6429; C12Y 304/21006; C12Y 304/21005
See application file for complete search history.

(56) References Cited

U.S. PATENT DOCUMENTS

| | | | | |
|---|---|---|---|---|
| 5,278,144 A | * | 1/1994 | Wolf ................... | C07K 14/745 424/94.64 |
| 5,583,107 A | | 12/1996 | Wolf et al. ................... | 514/13.7 |
| 5,635,481 A | | 6/1997 | Wolf ........................... | 514/20.1 |
| 5,650,314 A | | 7/1997 | Wolf ........................... | 435/219 |
| 5,795,863 A | | 8/1998 | Wolf ........................... | 604/890.1 |
| 2010/0178287 A1 | * | 7/2010 | Pryzdial ............... | A61K 31/727 424/94.64 |

OTHER PUBLICATIONS

Pryzdial, E.L.G., et al. 1996 The Journal of Biological Chemistry 27(28): 16614-16620.*
Li, D., et al. 2011 Colloids and Surfaces B: Biointerfaces 86: 1-6.*
Veronese, F.M. 2001 Biomaterials 22: 405-417.*
Ni, et al., "Increased thrombogenesis and embolus formation in mie lacking glycoprotein V." Blood. 98(2):368-73, 2001.
Pryzdial & Kessler, "Autoproteolysis or Plasmin-mediated Cleavage of Factor Xaa Exposes a Plasminogen Binding Site and Inhibits Coagulation" J Biolog Chem. 271(28):16614-20, 1996.
Sheffield, et al., "Reduction of thrombus size in murine models of thrombosis following administration of recombinant α1- proteinase inhibitor mutant proteins" Thrombosis and Haemostasis. 107:972-84, 2012.
Talbot, et al., "Enhanced fibrinolysis by proteolysed coagulation factor Xa" Biochimica et Biophyica Acta. 1804:723-30, 2010.
Talbot, et al., "Proteolytic modulation of factor Xa-antithrombin complex enhances fibrinolysis in plasma." Biochimica et Biophysica Acta. 1834(6):989-95, 2013.
Plyzdial et al.,*Journal of Thrombosis and Haemostasis* 14:1-11 (2016).

* cited by examiner

*Primary Examiner* — Marsha Tsay
(74) *Attorney, Agent, or Firm* — Norton Rose Fulbright US LLP

(57) ABSTRACT

The present disclosure provides a C-terminal tethered amino acid for modulating the thrombolytic, fibrinolytic and/or anticoagulant properties of a coagulation protein. The present disclosure also provides a coagulation protein having a catalytic site modified, either at the histidine or serine residue, with the C-terminal tethered amino acid as well as therapeutic applications of those modified coagulation proteins.

19 Claims, 8 Drawing Sheets

Time (Minutes)

Figure 9

C-TERMINALLY TETHERED AMINO ACIDS AND THEIR FIBRINOLYTIC THERAPEUTIC USES

CROSS-REFERENCE TO RELATED APPLICATIONS AND DOCUMENTS

This application claims priority from U.S. provisional patent application Ser. No. 61/834,613 filed on Jun. 13, 2013 and herewith incorporated by reference in its entirety. A sequence listing in computer readable format is being filed concurrently with this application and its content is incorporated by reference in its entirety.

TECHNOLOGICAL FIELD

This disclosure relates to coagulation proteins modified by a C-terminally-tethered amino acid, the stabilized fibrinolytic activity of the coagulation protein due to this modification, as well as the use of the coagulation protein associated with the C-terminally tethered amino acid as a fibrinolytic therapeutic.

BACKGROUND

A major cause of heart disease and stroke is the formation and persistence of aberrant clots that block the flow of blood. The predominant clot busting medicine is tissue plasminogen activator (tPA) and its recombinant derivatives. The main medical and commercial problems with tPA are that: 1) it may cause hemorrhage most likely because it is a functional enzyme exhibiting detrimental systemic effects; 2) about half of patients' clots are resistant to tPA and 3) it has only ~4% penetrance into the target market because of a finite time of efficacy (3-5 hours after the onset of symptoms).

It would be highly desirable to be provided with a safer therapeutic agent capable of accelerating the dissolution of a clot and/or preventing the formation of a clot. When used alone, the safer therapeutic agent would preferably have limited or no undesirable systemic effect (such as bleeding for example). When used in combination with known clot-busting medicine, the safer therapeutic agent would preferably increase the thrombolytic potential of the combined known clot-busting medicine, reduce the dose required of the known clot-busting medicine to observe beneficial therapeutic effects and ultimately limit the side effects associated with known clot-busting medicine.

BRIEF SUMMARY

The present disclosure provides a C-terminally tethered amino acid as well as its use in modulating the fibrinolytic/anticoagulant properties of a blood coagulation protein. Therapeutic uses associated with blood coagulation proteins chemically modified to be associated to the C-terminally tethered amino acid are also provided.

In accordance with the present disclosure there is provided a compound of formula

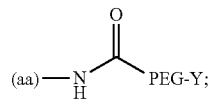

wherein,
(aa) is any amino acid less the amino group forming the amide linkage; PEG is 2-8 linear repeating units having the following formula

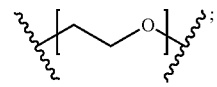

wherein each carbon atom of said unit is optionally substituted; Y is

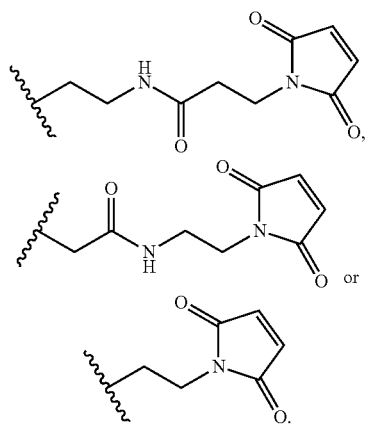

In an embodiment, the (aa) is a natural amino acid. In another embodiment, the (aa) is capable of binding to at least plasminogen, tPA or an additional fibrinolytic constituents. The (aa) can be, for example, lysine or alanine. In another embodiment, the PEG is —(CH$_2$—CH$_2$—O—)$_{2-8}$. In still another embodiment, the PEG is —(CH$_2$—CH$_2$—O—)$_{4-8}$. In yet a further embodiment, the PEG is —(CH$_2$—CH$_2$—O—)$_4$. In yet another embodiment, Y is

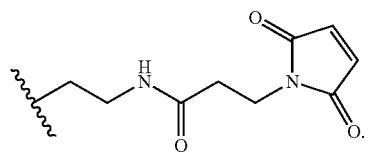 [SMILES: *CCNC(=O)CCN1C(=O)C=CC1=O]

In accordance with the present disclosure there is provided a compound of formula

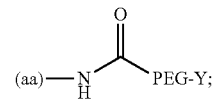

wherein, (aa) is lysine or alanine, Y is

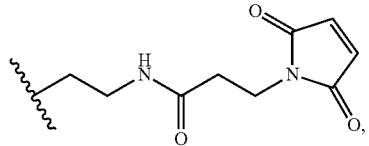

-continued

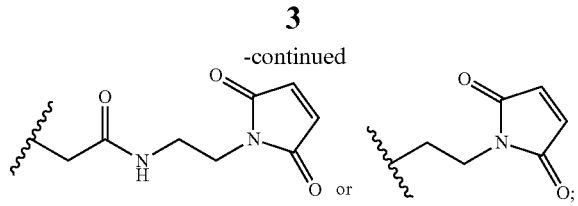

PEG is —(CH$_2$—CH$_2$—O—)$_4$. In yet another embodiment, Y is

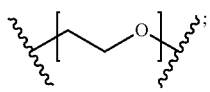

According to another aspect, the present disclosure provides a compound of formula

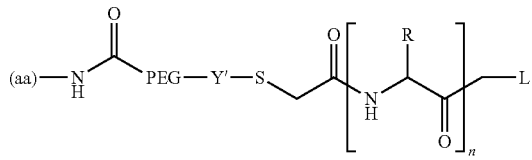

wherein (aa) is any amino acid less the amino group forming the amide linkage; PEG is 2-8 linear repeating units having the following formula

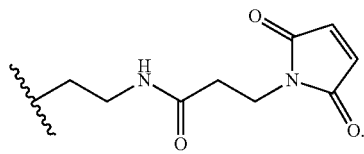

wherein each carbon atom of said unit is optionally substituted; and Y' is

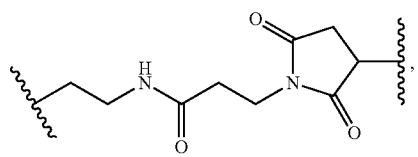

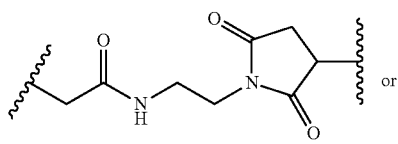

R is H or a residue of a natural or non-natural amino acid, L is a leaving group and n is an integer ranging from 2 to 4 (for example 3). In an embodiment, the (aa) is a natural amino acid. In another embodiment, the (aa) is capable of binding to at least plasminogen, tPA or an additional fibrinolytic constituents. The (aa) can be, for example, lysine or alanine. In another embodiment, the PEG is —(CH$_2$—CH$_2$—O—)$_{2-8}$. In still another embodiment, the PEG is —(CH$_2$—CH$_2$—O—)$_{4-8}$. In yet a further embodiment, the PEG is —(CH$_2$—CH$_2$—O—)$_4$. In an embodiment, Y' is

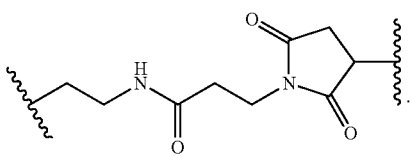 [SMILES: *CCNC(=O)CCN1C(=O)CC(*)C1=O]

In still another embodiment,

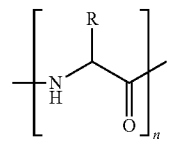

is (D)Phe-Pro-Arg-.

According to another aspect, the present disclosure provides a compound of formula

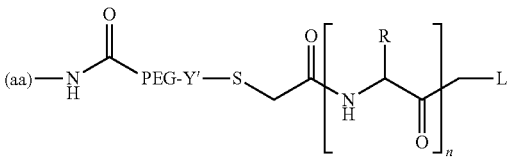

wherein (aa) is lysine or alanine; PEG is —(CH$_2$—CH$_2$—O—)$_4$; Y' is

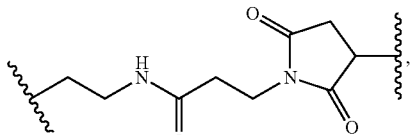

is (D)Phe-Pro-Arg- and L is a leaving group. In an embodiment of the above, Y' is

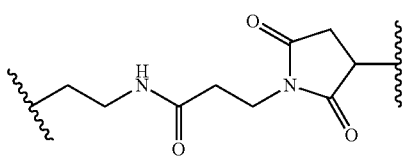 [SMILES: *CCNC(=O)CCN1C(=O)CC(*)C1=O]

and L is a halogen such as a chloride.

According to a further aspect, the present disclosure provides an isolated and modified blood coagulation protein, said blood coagulation protein being from the vitamin K-dependent family and having a modified histidine (His) or serine (Ser) residue of the following formula

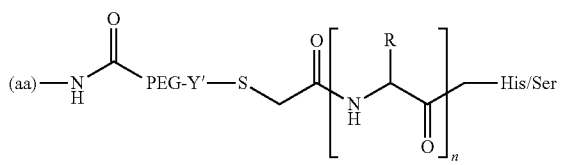

wherein (aa) and PEG are as defined as above; His/Ser is a histidine residue or a serine residue of the blood coagulation protein located within a serine protease active site, said His/Ser is covalently linked to the $CH_2$ moiety by the catalytic site imidazole-nitrogen atom of said histidine or hydroxyl of said serine; R is H or a residue of a natural or non-natural amino acid, n is an integer ranging from 2 to 4; and Y' is

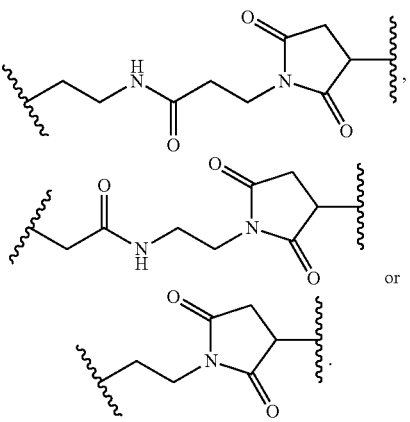

In an embodiment, the isolated and modified blood coagulation protein, has the following formula

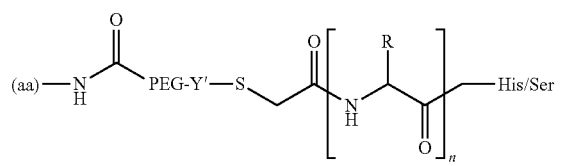

wherein (aa) is lysine or alanine; PEG is —$(CH_2$—$CH_2$—O—$)_4$; Y' is

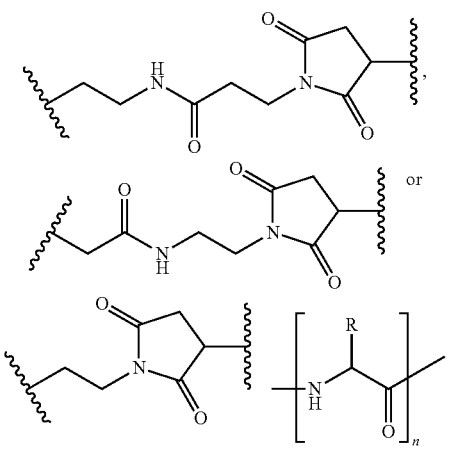

is (D)Phe-Pro-Arg-. In an embodiment of the above, Y' is

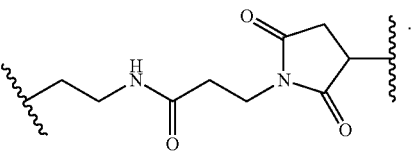 [SMILES: *CCNC(=O)CCN1C(=O)CC(*)C1=O ; "."]

In an embodiment, the blood coagulation protein is a human protein and/or can be isolated from blood or a blood derivative. In still a further embodiment, the blood coagulation protein is a FXa protein. In yet another embodiment, the FXa protein has (i) a light chain having an amino acid sequence as set forth at positions between 41 to 179 of SEQ ID NO: 1 or 2 and (ii) a heavy chain having an amino acid sequence as set forth in at positions between 235 to 467, between 235 to 469, between 235 to 473, between 235 to 475, between 235 to 487, or between 235 to 488 of SEQ ID NO: 1 or 2.

In still a further embodiment, the isolated and modified blood coagulation protein, has the following formula

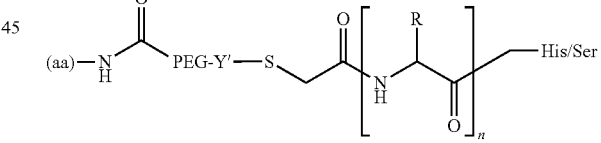

wherein (aa) is lysine or alanine; PEG is —$(CH_2$—$CH_2$—O—$)_4$; Y' is

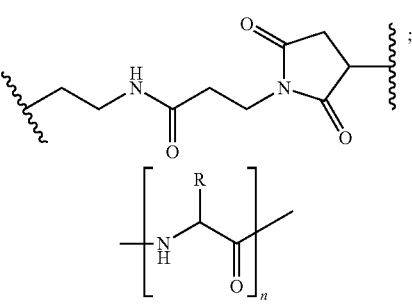

is (D)Phe-Pro-Arg- and the blood coagulation protein is a FXa protein that has (i) a light chain having an amino acid sequence as set forth at positions between 41 to 179 of SEQ ID NO: 1 or 2 and (ii) a heavy chain having an amino acid sequence as set forth in at positions between 235 to 467, between 235 to 469, between 235 to 473, between 235 to 475, between 235 to 487, or between 235 to 488 of SEQ ID NO: 1 or 2.

According to another aspect, the present disclosure also provides a combination of a plurality of isolated and modified blood coagulation protein as defined above and comprising at least one isolated and modified FXa having, as a heavy chain, an amino acid sequence as set forth in at positions between 235 to 487 or between 235 to 488 of SEQ ID NO: 1 or 2; at least one isolated and modified FXa having, as a heavy chain, an amino acid sequence as set forth in at positions between 235 to 467, between 235 to 473 or between 235 to 475 of SEQ ID NO: 1 or 2; and at least one isolated and modified FXa having, as a heavy chain, an amino acid sequence as set forth in at positions between 235 to 469.

According to yet another aspect, the present disclosure provides a process for obtaining the isolated and modified blood coagulation protein as defined above. Broadly, the process comprises (a) providing an isolated blood coagulation protein of the vitamin K-dependent family having a histidine (His) or serine (Ser) residue in a serine protease active site; (b) reacting said blood coagulation protein with a compound of formula

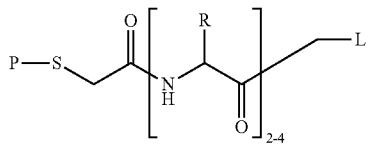

wherein P is a protecting group, R is H or a residue of a natural or non-natural amino acid and L is a leaving group, wherein said L can be substituted by the His or Ser residue of the blood coagulation protein located within the active site; (c) removing said protecting group P after step (b) and (d) reacting the product of step (c) with the compound as defined above and (e) isolating said modified blood coagulation protein.

According to yet another embodiment, the present disclosure provides a process for obtaining the isolated and modified blood coagulation defined above. Broadly, the process comprises (a) providing an isolated blood coagulation protein of the vitamin K-dependent family having a histidine (His) or serine (Ser) residue in a serine protease active site; (b) reacting said blood coagulation protein with a compound of formula

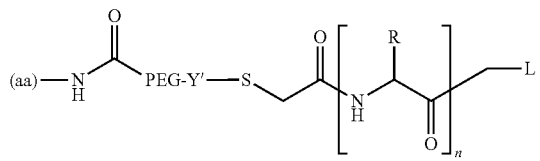

wherein (aa), PEG, and R are as defined above, L is a leaving group, n is an integer of 2 to 4; and Y' is

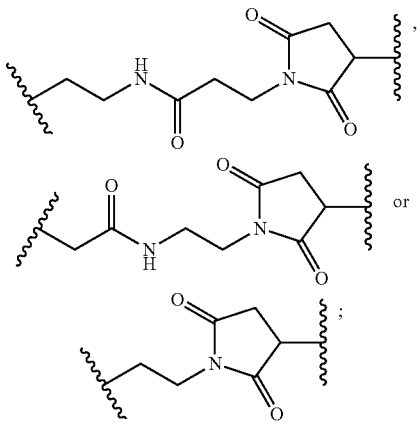

and (c) isolating said modified blood coagulation protein.

According to another aspect, the present disclosure provides a pharmaceutical composition comprising the isolated modified blood coagulation protein described herein or the combination described herein and a pharmaceutically acceptable excipient. In an embodiment, the pharmaceutical composition further comprises a thrombolytic agent (such as, for example, tissue plasminogen activator, a tissue plasminogen activator variant, urokinase and/or streptokinase). In yet a further embodiment, the tissue plasminogen variant activator is tenecteplase. In another embodiment, the pharmaceutical composition further comprises an anticoagulant, such as, for example, heparin.

According to still a further aspect, the present disclosure provides a method for dissolving a clot in a subject in need thereof. Broadly, the method comprises administering a therapeutic effective amount of the isolated modified blood coagulation protein of described herein, the combination described herein or the pharmaceutical composition described herein to the subject so as to dissolve the clot.

According to still a further aspect, the present disclosure provides the use of the isolated modified blood coagulation protein described herein, the combination described herein or the pharmaceutical composition described herein for dissolving a clot in a subject, such as, for example a mammalian subject (e.g., a human).

According to another aspect, the present disclosure provides a method of improving the therapeutic property of a thrombolytic agent. Broadly, the method comprises administering a therapeutic effective amount of the isolated modified blood coagulation protein described herein, the combination described herein or the pharmaceutical composition described herein with the thrombolytic agent to the subject. In an embodiment, the thrombolytic agent is administered at a dose considered sub-therapeutic when used in the absence of the pharmaceutical composition. In another embodiment, the thrombolytic agent is administered at a timing considered sub-therapeutic when used in the absence of the pharmaceutical composition. In an embodiment, the pharmaceutical composition the thrombolytic agent is, for example, tissue plasminogen activator, a tissue plasminogen activator variant, urokinase and/or streptokinase. In yet a further embodiment, the tissue plasminogen variant activator is tenecteplase.

According to a further aspect, the present disclosure provides the use of the isolated modified blood coagulation protein described herein, the combination described herein or the pharmaceutical composition described herein for improving the therapeutic property of a thrombolytic agent in a subject, such as a mammalian subject (e.g., a human). In an embodiment, the thrombolytic agent is adapted for administration at a dose considered sub-therapeutic when used in the absence of the modified blood coagulation protein, the combination or the pharmaceutical composition. In another embodiment, the thrombolytic agent is adapted for administration at a timing considered sub-therapeutic when used in the absence of the modified blood coagulation protein, the combination or the pharmaceutical composition. In yet another embodiment, the thrombolytic agent is selected from the group consisting of tissue plasminogen activator, a modified tissue plasminogen activator, urokinase and streptokinase. In yet another embodiment, the modified tissue plasminogen activator is tenecteplase.

BRIEF DESCRIPTION OF THE DRAWINGS

Having thus generally described the nature of the disclosure, reference will now be made to the accompanying drawings, showing by way of illustration, a preferred embodiment thereof, and in which:

Figure 9:
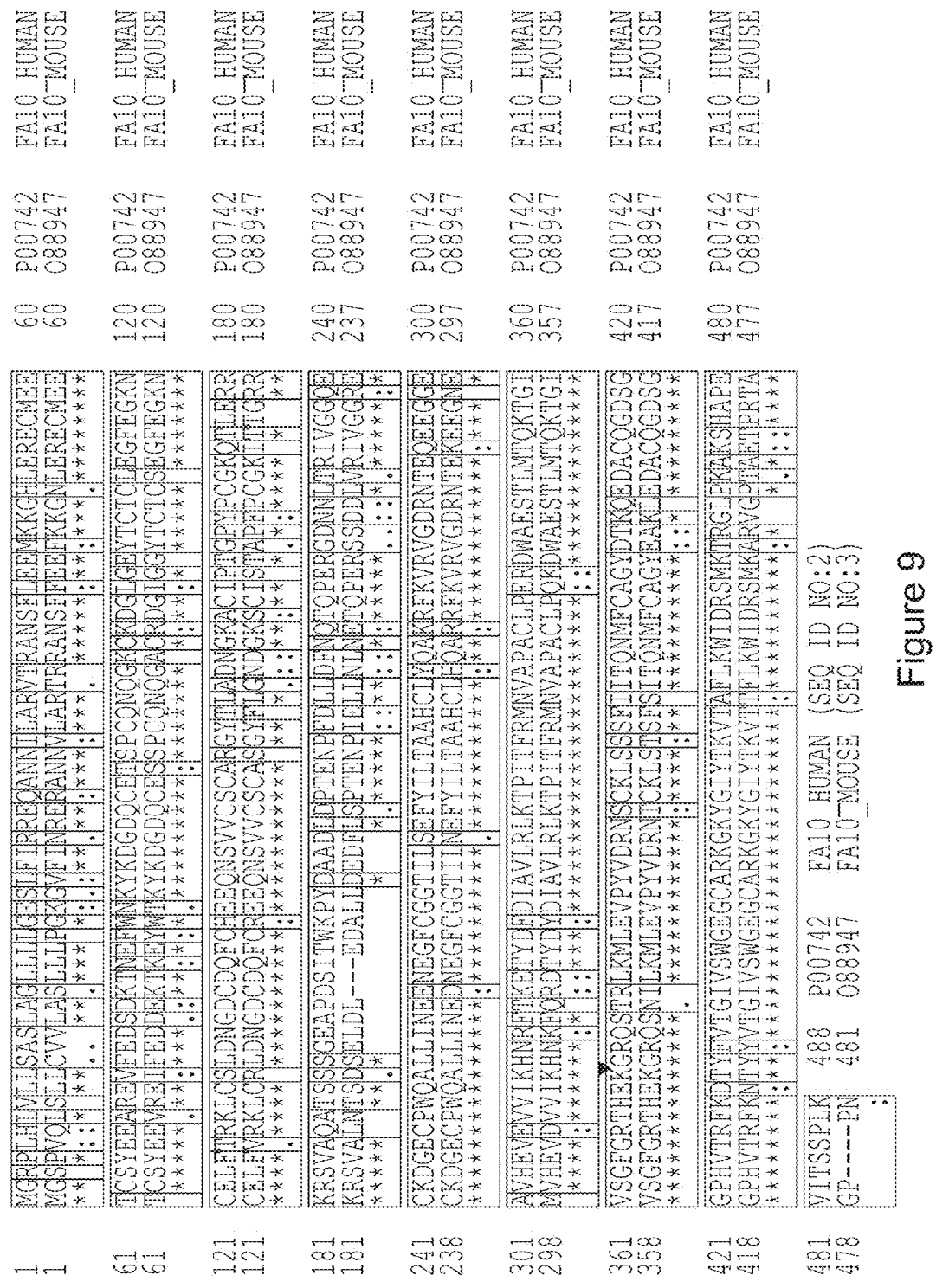

FIG. 9 illustrates that mouse FXa has amino acids identical to human FXa at the Xa33/13 cleavage site. "*" are identical amino acids, ":" are conserved amino acids, "filled triangle" indicates the site cleaved by plasmin to convert human FXaβ to Xa33/13 and "open triangles" indicate possible cleavage sites by plasmin to render human FXaβ. Note the signal peptide and propeptide are shown in the alignment. Uniprot was used for the alignment.

DETAILED DESCRIPTION

Figure 1:
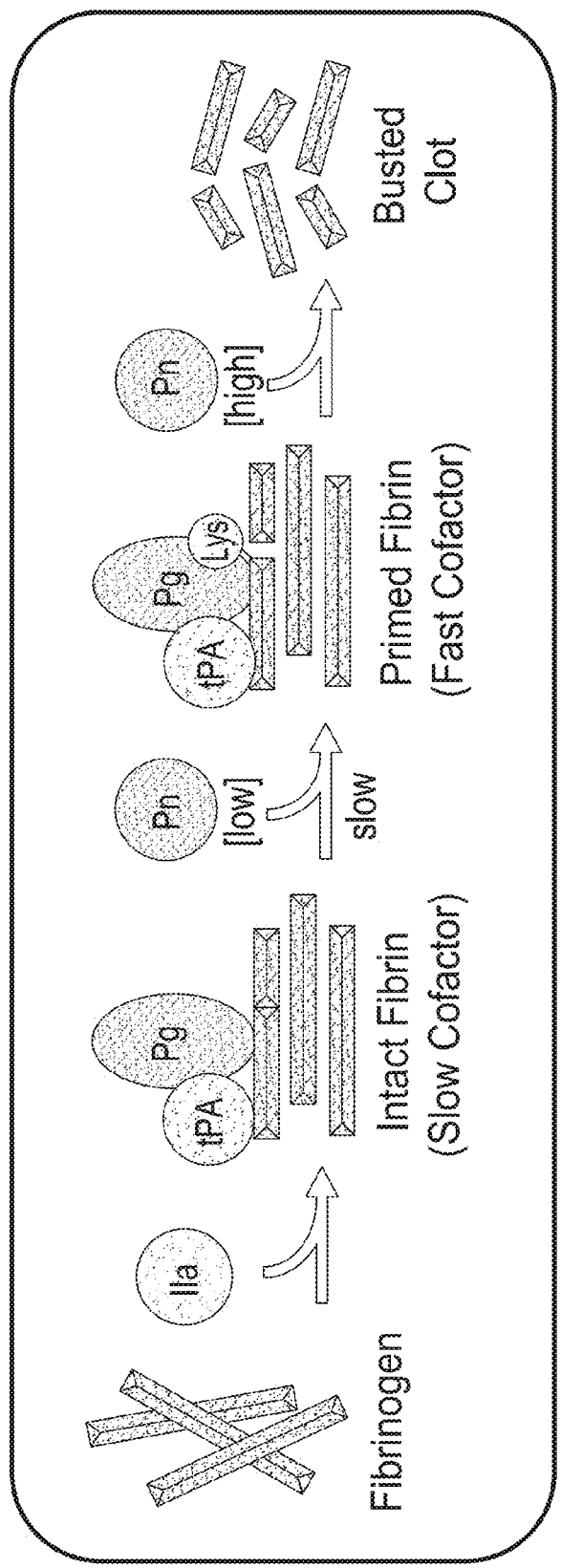
FIG. 1 illustrates a classical model of fibrinolysis, in which IIa=thrombin, tPA=tissue plasminogen activator, Pg=plasminogen, Pn=plasmin, Lys=C-terminal Lysine.

As known in the art and depicted in FIG. 1, thrombin (IIa) initiates clot formation, in which the molecular scaffolding is fibrin. Once the clot has served its purpose to seal leaky vasculature, the fibrinolysis pathway dissolves it. The prevailing "classical" model of fibrinolysis is that fibrin controls clot-busting by accelerating tissue plasminogen activator (tPA). This cofactor function of fibrin has two chemically distinct phases. In the first (slow) phase, binding sites on intact fibrin bring together tPA and plasminogen (Pg) resulting in the first molecules of plasmin (Pn). Plasmin cuts the clot, but this initial plasmin production is believed to be inadequate to overcome the normal level of plasma inhibitors. Nevertheless, this low amount of plasmin slowly cleaves the fibrin, and primes it for participating in the second (fast) phase of tPA cofactor function by exposing C-terminal lysines (or CTK, where K is the conventional single letter abbreviation) on the cleaved fibrin. These CTK provide new binding sites for tPA and Pg activation. Thus, primed fibrin (e.g. having exposed CTKs) is an enhanced tPA cofactor that ultimately increases plasmin generation beyond the intrinsic anti-fibrinolysis threshold, enabling the clot to dissolve.

Based on the general understanding in the art that the vast concentration of fibrin would overwhelm the potential contribution of any other proteins in the vicinity of a clot, it is thus believed that fibrin is the only required tPA cofactor. However, as described herein a chemically-modified blood coagulation protein, having an inactive serine protease catalytic site was shown to act as a tPA cofactor and, in the vicinity of a clot, accelerated clot dissolution. The purified and chemically-modified blood protein was found to mediate tPA cofactor activity, and, in some embodiment, bind to plasminogen, tPA or other fibrinolytic constituents.

One of the advantages of the chemically-modified blood protein described herein, when compared to tissue plasminogen accelerator (tPA), is that it does not involve administration of a proteotically functional enzyme thus limiting systemic effects, such as those observed with tPA or its variants. Furthermore, currently, tPA must be administered within a short period after the onset of symptoms (3 to 5 hours), possibly because maturation of the clot may prevent it from undergoing proteolysis to expose C-terminal amino acids (or CTAA such as, for example, CTK), thereby it cannot easily be "primed" to become a "fast" cofactor, as illustrated in FIG. 1. Many patients who could benefit from clot-busting therapy are excluded from treatment due to this finite timeframe. As it will also be shown below, the chemically modified blood coagulation protein stabilizes its effectiveness as a fibrinolysis cofactor, which may be useful to extend the opportunity to treat a patient with a therapeutic thrombolytic agent after the onset of symptoms.

Without wishing to be bound to theory, the experimental evidence provided herein suggests an "auxiliary cofactor" model of fibrinolysis in which the initial phase of plasmin production is augmented by the modified blood coagulation protein exhibiting increased and constitutive tPA cofactor activity. The CTAA-modified blood coagulation protein is more susceptible than fibrin to "priming" by plasmin and consequently it acquires additional CTK more quickly than fibrin to initially accelerate tPA.

C-Terminal Tethered Amino Acid Moiety

The present disclosure provides a C-terminal tethered amino acid which can be attached to at least one of the amino acids of the catalytic active site of a serine protease to modulate its biological activity.

In one embodiment, there is therefore provided a compound of formula;

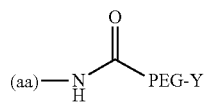

wherein (aa)-NH is an amino acid PEG is polyethylene glycol and Y provides linkage to a coagulation protein.

In one embodiment, there is further provided a compound of formula

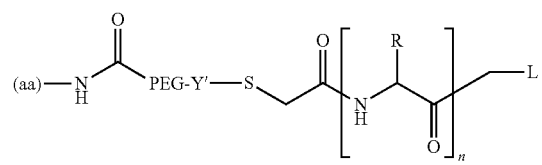

wherein (aa), PEG, Y', R, L and n are as defined above.

In one embodiment, (aa) is any naturally occurring or natural amino acid (such as alanine, cysteine, aspartic acid, glutamic acid, phenylalanine, glycine, histidine, isoleucine, lysine, leucine, methionine, asparagine, proline, glutamine, arginine, serine, threonine, valine, tryptophan or tyrosine). In another embodiment, (aa) is a D-version of an amino acid. In still another embodiment, (aa) is a modified and/or unusual amino acid (such as, for example 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine or ornithine). In an embodiment, the tethered (aa) is capable of facilitating binding to at least plasminogen, tPA or any other fibrinolytic constituents (such as, for example, tPA variants, fibrin). In a preferred embodiment, the (aa) is lysine or alanine.

For greater clarity, what is meant by (aa) is an amino acid "less the amino group forming the amide linkage" is intended to avoid duplicating the amino group involved in the amide bond. The following scheme illustrates the group connectivity for a lysine wherein PEG is PEG of 4 subunits:

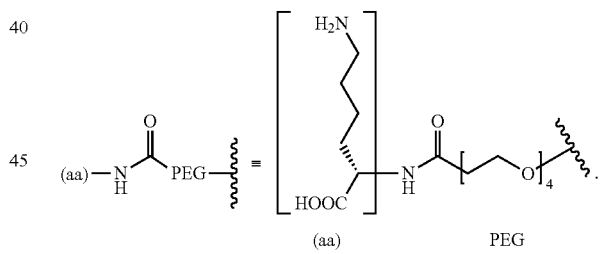

The length of —(CO)-PEG-Y'— or —(CO)-PEG-Y is designed to allow the CT(aa) to protrude from the modified blood coagulation protein onto which it is bound and, ultimately, be accessed by Pg and/or tPA. For example, the length of —(CO)-PEG-Y'— or —(CO)-PEG-Y— can be selected to be at least about 20 Å as depicted below.

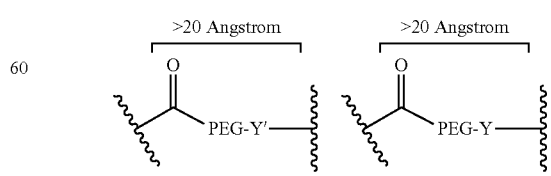

The skilled person is able to determine the required PEG depending on the desired length of —(CO)-PEG-Y'— or —(CO)-PEG-Y— as well as the nature of Y' or Y. The length of —(CO)-PEG-Y'— or —(CO)-PEG-Y— is preferably less than about 40 Å. Such length is believe not to interfere with the binding of anionic phospholipid and potential cleavage that could expose a Pg binding site in the coagulation protein itself. In an embodiment, when the tethered amino acid is used to modify the blood coagulation protein (FXa for example), the spacer is believe to minimize interference at the C-terminus of the blood coagulation protein (FXa's heavy chain for example), thereby allowing the removal the β-peptide thus exposing tPA/plasminogen binding site(s). However, the active site modification spacer length are sufficient to prevent cleavage of FXa in the autolysis loop to inhibit production of Xa33/13 by plasmin or in plasma.

In an embodiment, the PEG is 2-8 linear repeating units having the following formula wherein each carbon atom of said unit is optionally substituted. In some embodiments, PEG may be a mixture of n=2-8. In some embodiments, PEG (and its substituted derivatives) can be branched. In certain embodiments, PEG is wherein the PEG is $—(CH_2—CH_2—O—)_{2-8}$, alternatively PEG is $—(CH_2—CH_2—O—)_{4-8}$ alternatively PEG is $—(CH_2—CH_2—O—)_4$. The particular PEG derivatives listed above are exemplary only, and the disclosure is not intended to be limited to those particular examples.

Considering the feature described above with regard to the length of —(CO)-PEG-Y'— or —(CO)-PEG-Y, it becomes conceivable that Y be any stable maleimide residue suitable for the Michael addition of a thiol (—SH). Y may be described by the general formula:

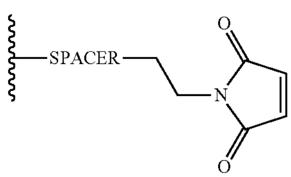

wherein spacer is linear chain comprising 0-6 atoms, preferably carbon atoms, such as alkylene, said chain can be interrupted by one or more non-consecutive heteroatoms (such as O and N) or by an arylene, amido (—NH—(CO)— or —(CO)NH—), ester (—(CO)O— or —O(CO)—) and the chain is optionally substituted by one or more substituent such as halo, amino, hydroxyl, oxo (C═O).

In one embodiment, Y is

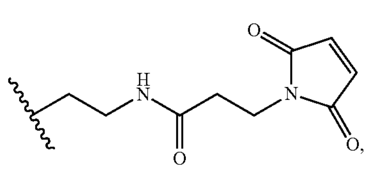

-continued 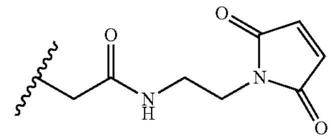 or

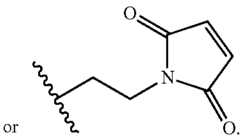

In one embodiment, Y is

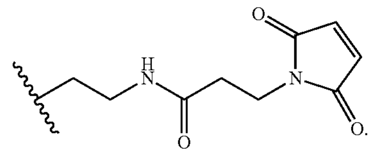 [SMILES: *CCNC(=O)CCN1C(=O)C=CC1=O]

The following scheme illustrates the group connectivity between a PEG4 residue and a representative Y group:

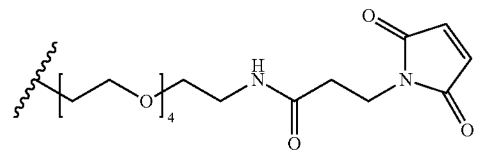

In one embodiment, Y' is 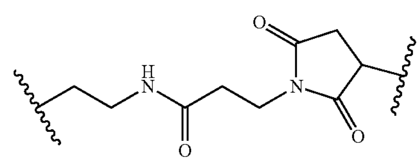 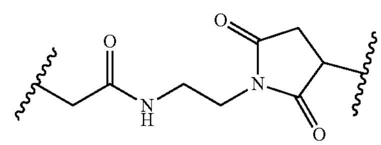 or

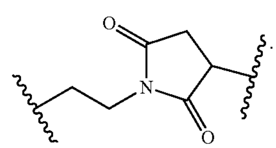

In one embodiment, Y' is

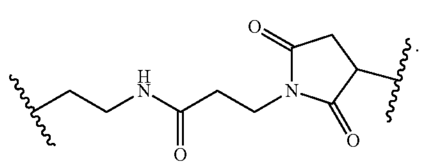 [SMILES: *CCNC(=O)CCN1C(=O)CC(*)C1=O]

In one embodiment of the compound defined above,

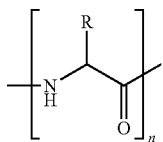

is a di-, tri- or tetra-peptide having sufficient affinity to the active site of a blood coagulation protein. In one embodiment, n is 3. In one embodiment, the tripeptide is Phe-Pro-Arg- or preferably (D)Phe-Pro-Arg-. It is also contemplated that analogs of Phe-Pro-Arg- can be used. In particular, mimics of one or more of each aminoacid can be used. Alternatively, mimics of two amino acids can be used. Examples of such suitable mimics are known in the art.

In one embodiment of the compound defined above, L is a leaving group, wherein said L can be substituted by the His or Ser residue of the blood coagulation protein located within the active site. The leaving groups suitable to react with said His or Ser residue are known in the art. For example, a halogen such as a chloride may be suitable. Essentially, it is believed that the leaving group L will be substituted by the nucleophilic nitrogen or oxygen of the active site e.g.

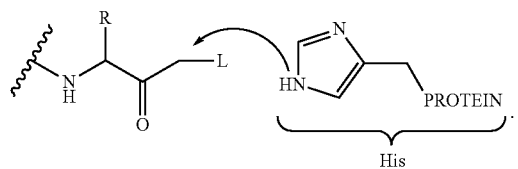

The present disclosure further provides an exemplary process for making the compound of formula

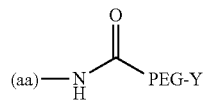

comprising reacting a compound of formula

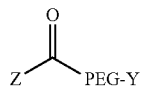

with an amino acid (aa)-$NH_2$ under suitable conditions; wherein (aa) is an amino-acid (less the amino group that will be part of the amide bond) as defined above or a protected amino acid, PEG and Y are as defined above and Z is HO— or a carboxyl activating group suitable for forming a peptide bond. It will be appreciated that when Z is HO—, a coupling reagent will preferably be used to form the amide bond. Z is preferably a carboxyl activating group such as a N-hydroxysuccinimide or a derivative thereof.

The present disclosure further provides an exemplary process for making the compound of formula

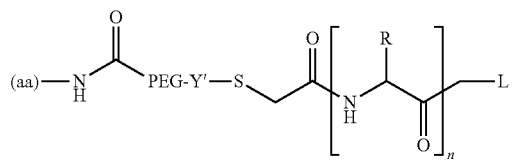

comprising reacting a compound of formula

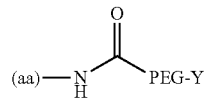

as defined herein, in accordance with the following schemes

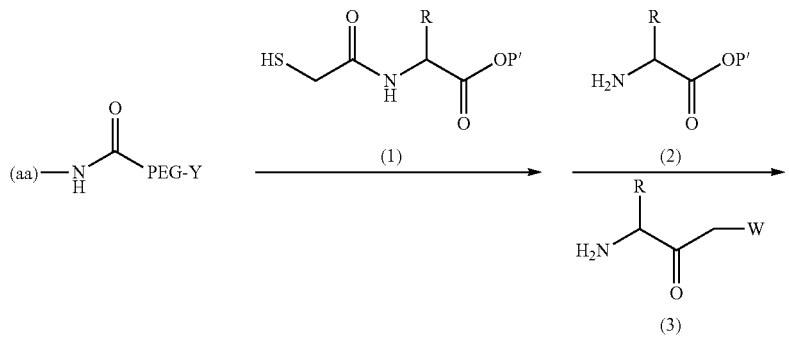

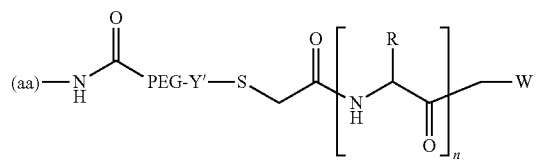

In the above scheme, the thiol (—SH) of compound (1) can react in a Michael addition with Y to form a first intermediate (not shown). Compound (2) is then coupled with the first intermediate up to two times (depending on whether n is 3 or 4) using standard amide coupling protocols to form a second intermediate (not shown). If n=2, then compound (2) is not coupled to the first intermediate. In compounds (1) and (2), and P' is independently either H, a protecting group or an activating group as well known and used in the art of peptide coupling. Compound (3) is then coupled with the second intermediate using standard amide coupling protocols. In compounds (1), (2) and (3), R is as defined herein. In the above scheme, W is either the leaving group L as defined above or a precursor of L. A precursor of the leaving group L is well known. For example, an —OH residue can be transformed, in accordance with known method, into a sulfonate of halogen (such an chloride).

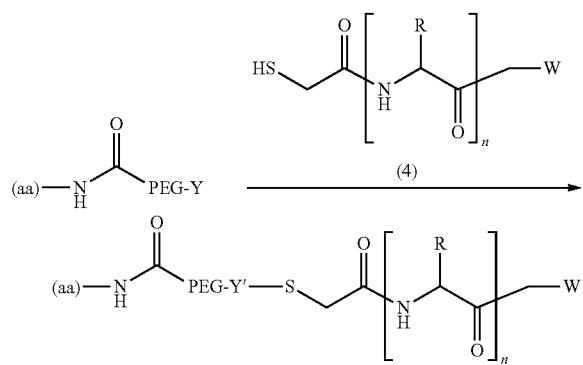

In the above scheme, the thiol (—SH) of compound (4) can react in a Michael addition with Y to form the desired compound wherein R is as defined herein and W is either the leaving group L as defined above or a precursor of L. As discussed above, the precursor of the leaving group L can be prepared in accordance with known methods.

C-Terminal Tethering of Blood Coagulation Proteins

The C-terminal tethered amino acids described herein can be used to modify blood coagulation proteins to modulate their thrombolytic, fibrinolytic and/or anticoagulant properties. As it will be shown and discussed herein, the addition of the C-terminal tethered amino acid to the serine protease active site of a blood coagulation protein increases its thrombolytic and/or anticoagulant property. Further, such modification limits the systemic activation of fibrinolysis which can be observed upon the administration of non-modified blood coagulation proteins.

As used herein, the term "thrombolysis" refer to the act of dissolving a blood clot that renders clinical symptoms and the term "thrombolytic" refers to the ability of dissolving the pathological clot a (i.e. thrombus). A therapeutic agent is believed to have thrombolytic activity (e.g., capable of mediating thrombolysis) when its presence is associated with a decrease in the time to dissolve a blood clot (as measured, for example, by the half-time required to dissolve a blood clot) when compared to a placebo (e.g., a control agent having no thrombolytic properties). In some embodiments, thrombolytic activity should be localized to the vicinity of a clot to avoid systemic side effects, such as hemorrhage.

As used herein, the term "fibrinolysis" refers to the act of enzymatically cleaving fibrin present in a blood clot (e.g., insoluble fibrin) and the term "fibrinolytic" refers to the ability of enzymatically cleaving clot-associated fibrin. The term "systemic fibrinolysis" in the context of the present disclosure refers to a state in which fibrin or soluble fibrinogen is enzymatically cleaved outside the clot (e.g., in a soluble form). A state of systemic fibrinolysis can cause clinical symptoms and unwanted side effects such as abnormal bleeding (and in some embodiments hemorrhage). It is understood that in the context of the present disclosure, "systemic fibrinolysis" should be limited and preferably avoided.

The term "anticoagulant", as used in the context of the present disclosure, refers to the ability to retard or inhibit the formation of a blood clot. A therapeutic agent is believed to have anticoagulant activity when its introduction into blood that is induced to clot is associated with an increase in the coagulation time (as measured, for example, by thromboelastography) when compared to a placebo (e.g., a control agent having no anticoagulant properties).

As it will be shown below, the current disclosure provides experimental evidence on the modification of the coagulation protein FXa as a proof-of-concept example, but does not intend to exclude other possible serine proteases with similar fibrinolytic application after modification by this procedure. More particularly, the C-terminal tethered amino acids are especially useful to modify the blood coagulation serine proteases of the vitamin K-dependent family to modify their fibrinolytic, thrombolytic and/or anticoagulant properties. As indicated above, the C-terminal tethered amino acids (CTAA) are specifically added to a histidine residue or a serine residue located within the serine protease active site. In some embodiments, the CTAA-addition may increase pre-existing thrombolytic and/or fibrinolytic activity. In other embodiments, the CTAA-addition may confer a thrombolytic and/or fibrinolytic activity function to the coagulation serine protease. In additional embodiments, the addition can establish or improve anticoagulant properties to the blood coagulation protein. In further embodiments, the chemical addition limits the proteolytic cleavage of the blood coagulation protein into its typical fragments observed in plasma, thereby extending its therapeutic effects.

Vitamin K is an essential cofactor to a hepatic gamma-glutamyl carboxylase that adds a carboxyl group to glutamic acid residues on several blood coagulation proteins: factors II (prothrombin), VII, IX and X, as well as Protein S, Protein C and Protein Z. These proteins (factors II, VII, IX and X, as well as Protein S, Protein C and Protein Z) are collectively referred to as members of the vitamin K-dependent family. It is worth noting that Protein S and Protein Z do not have a serine protease catalytic site and as such cannot be similarly modified to include the CTAA described herein. As such, in the context of the present disclosure, it is contemplated that the vitamin K-dependent blood coagulation proteins that bear a modification, in their catalytic site, with a CTAA include factors II (prothrombin), VII, IX and X, as well as Protein C.

Some of the members of this family (factors II, VII, IX and X) are enzymatically processed, from single polypeptides, into two-polypeptide proteins having each a light and a heavy chain. Other members of this family remain as single-polypeptide proteins (Protein C). In an embodiment, the members of the vitamin K-dependent family of coagulation proteins includes two-polypeptide proteins and exclude single-polypeptide proteins (such as protein C).

Coagulation proteins of the vitamin K-dependent family, during the resolution of a clot, can be submitted to further proteolytic processing into fragments which, in the mammalian circulation, may have limited or no thrombolytic and/or anticoagulant activity. The members of the vitamin K-dependent coagulation proteins are known by those skilled in the art to be well conserved, amongst the mammalian species. As such, results obtained with a particular mammalian species (for example a rodent such as a mouse) are indicative that similar results are expected in another mammalian species (for example a human). In addition, and still based on the similarity between the proteins amongst mammalian species, it is also possible to use, as a source of coagulation protein, a protein originating from a specific mammalian species (for example a human) and use it successfully in another mammalian species (for example a rodent such as a mouse) to mediate its biological activity.

Exemplary members of this family as well as some of their key amino acid characterization are listed in Table A below.

TABLE A

Vitamin-K dependent coagulation proteins characterization. Amino acid numbering is based on UniProt ID. H = histidine.

| Protein | UniProt ID | Single chain | Light chain | Heavy chain | Putative residues involved in light/heavy chain bond | Position of H in serine protease active site | Position of S in serine protease active site |
|---|---|---|---|---|---|---|---|
| Human Factor IIa | P00734 | — | 328-363 | 364-622 | 336/482 | 406 | 568 |
| Mouse Factor IIa | P19221 | — | 325-360 | 361-618 | 333/479 | 403 | 565 |
| Human Factor VIIa | P08709 | — | 61-212 | 213-466 | 195/322 | 253 | 404 |
| Mouse Factor VIIa | P70375 | — | 42-193 | 194-446 | 176/303[1] | 234 | 379 |
| Human Factor IXa | P00740 | — | 47-191 | 227-461 | 178/335 | 267 | 411 |
| Mouse Factor IXa | P16294 | — | 47-192 | 237-471 | 178/345[1] | 277 | 421 |
| Human FXa | P00742 | — | 41-179 | 235-467, 235-469, 235-473, 235-475, 235-487, or 235-488 | 172/342 | 276 | 419 |
| Mouse FXa | O88947 | — | 41-180 | 232-481, 232-464, or 232-466 | 172/339 | 273 | 416 |
| Human Protein C | P04070 | — | 43-197 | 212-461 | 183/319 | 253 | 402 |
| Mouse Protein C | P33587 | — | 42-196 | 213-460 | 182/319 | 253 | 401 |

[1]by similarity to human

One of the exemplary members of the vitamin K-dependent coagulation protein is FX. Human FX has been extensively studied and characterized. Mouse FX has 89% amino acid sequence similarity to human FX and therefore is known to have similar coagulation function to the human protein. Human FX has the amino acid sequence presented in Uniprot ID P00742 (SEQ ID NO: 1 and SEQ ID NO: 2). In circulation, the two chain polypeptide encoding human FX is processed into a light chain and a heavy chain, associated via a disulfide bond. After activation to FXa, at the site of vacular damage, human FXa is present in various and distinct forms:

FXaα protein. This protein has, as a light chain, the amino acid residues spanning positions 41 to 179 of Uniprot ID P00742 and, as a heavy chain, the amino acid residues spanning positions 235 to 487 or positions 235 to 488 of Uniprot ID P00742 (Pryzdial et al., 1996).

FXaβ protein. The FXaβ proteins result from the proteolytic cleavage of FXaα protein at the C-terminus. All FXaβ proteins have, as a light chain, the amino acid residues spanning positions 41 to 179 of Uniprot ID P00742. Some FXaβ proteins are able to bind to plasminogen and because of this are deduced to have, as a heavy chain remnant the amino acid residues spanning positions 235 to 467, 235 to 473 or 235 to 475 of Uniprot ID P00742. Plasminogen-binding FXaβ are obtained via the proteolytic cleavage of the FXaα protein, in the presence of a procoagulant phospholipid-containing membrain (proPL; e.g., phosphatidyl serine) and calcium. Another form of FXaβ exists and it is not able to bind to plasminogen. This form is deduced to have, as a heavy chain remnant the amino acid residues spanning positions 235 to 469 of Uniprot ID P00742. These FXaβ proteins are obtained via the proteolytic cleavage of the FXaα protein, in the absence of proPL, in the presence of a calcium chelator, such as ethylenediamine tetraacetic acid or in the absence of calcium.

FXa fragments. In the presence of plasmin, the FXaβ proteins can be further cleaved into distinct fragments:

FXa33 and FXa13 fragments. When the plasminogen-binding FXaβ is proteolytically processed by plasmin or possibly other enzymes in plasma, its heavy chain is cleaved, between residues 370 and 371 of Uniprot ID P00742, generating an ~33 kDa fragment (referred to as FXa33) and an ~13 kDa fragment (referred to as FXa13). The FXa33 fragment still retains the light chain (amino acid residues spanning positions 41 to 179 of Uniprot ID P00742) disulfide-linked to a heavy chain fragment (amino acid residues spanning positions 235 to 370 of Uniprot ID P00742). The FXa13 only comprises a fragment of the heavy chain (amino acid residues spanning positions 371 to 467, 371 to 473 or 371 to 475 of Uniprot ID P00742).

FXa40 fragment. When the FXaβ protein, which is not capable of binding to plasminogen is proteotically processed, its light chain is cleaved at a position between amino acid residue 89 and 90 of Uniprot ID P00742. The FXa40 fragment thus comprises a light chain (amino acid residues spanning positions 84 to 179 of Uniprot ID P00742) covalently attached to a heavy chain (amino acid residues spanning 235 to 469 of Uniprot ID P00742).

Mouse FX has the amino acid sequence presented in Uniprot ID O88947 (SEQ ID NO: 3 and SEQ ID NO: 4). Similar to the human ortholog, mouse FXa protein is a light chain and a heavy chain, covalently associated via a disulfide bond. The light chain spans amino acid residues between positions 41 to 180, whereas the heavy chain spans amino acid residues between 232 and 481 of Uniprot O88947. It is unknown if the intact mouse FXa (FXaα) undergoes C-terminal proteolysis to form FXaβ, like human, although several identical amino acids exist that would render mouse heavy chains spanning amino acids 232-466 and 232-464. The latter would be predicted to bind plasminogen. A FX-derived 33 kDa fragment was furthermore observed in mouse plasma. Since there are identical amino acids as those spanning the human cleavage site this may yield a mouse counterpart consisting of the intact light chain disulfide linked to the remnant of the heavy chain consisting of amino acids 232-367, possibly capable of binding plasminogen.

In the context of the present disclosure, the coagulation protein to be modified can be isolated from plasma. In an alternative embodiment, the coagulation protein to be modified can also be obtained from a recombinant source. In an embodiment, the isolated coagulation proteins to be modified will comprise a population of coagulation proteins showing heterogeneity at the C-terminal end of the heavy chain. Alternatively, the coagulation proteins isolated/obtained under conditions to allow the maintenance/enrichment of one of the forms of the coagulation protein or, in some embodiment, to select only one of the forms of the coagulations proteins. For example, in some embodiments, it may be beneficial to isolate/obtain the FXa protein in the FXaα form or just one of the FXaβ forms. The various forms of the coagulation proteins that are amenable to chemical modification as described herein are shown in Table A.

The main biological function of the members of the vitamin K-dependent family which have a serine protease catalytic site is to selectively cleave target polypeptides. Within the catalytic active site of those members, three amino acids (His, Asp, Ser) have been identified as responsible for this enzymatic activity. It is believed that the modification of the histidine or the serine residue present in the catalytic site with the C-terminal tethered amino acid limits (and in some embodiments prevents) the serine protease activity of the modified coagulation proteins. At the same time, in some embodiments, the CTAA-modification of the active site increases or bestows thrombolytic activity, increases or bestows fibrinolytic activity and/or bestows anticoagulant activity of the modified proteins. Further, in additional embodiment, the CTAA-modification of the active impedes (and in some embodiments inhibits) the proteolytic cleavage of the coagulation protein into smaller fragments.

Since it is possible that more than one form of the coagulation protein be isolated/obtained and subjected to chemical modification to attach the C-terminal tethered modified amino acid, the present disclosure also provides a combination of modified coagulation proteins. This combination of modified coagulation proteins includes a type of coagulation proteins (FXa for example) but more than one form of the coagulation protein (FXaα and FXaβ and Xa33/13 for example).

In one specific embodiment, there is provided a chemically modified version of clotting FXa which has been modified with a CTK, designated Xa-K. Xa-K has clot-busting (i.e. thrombolytic) and clot-stopping (i.e. anticoagulant) activity. The addition of a CTK to the catalytic site of FXa improves its clot-busting activity, while blocking its coagulant activity. The addition of a CTK also limits (e.g., inhibits) additional proteolytic cleavage of FXaβ by purified plasmin and in plasma Pharmaceutical Compositions and Therapeutic Uses The modified coagulation proteins disclosed herein can be formulated into a pharmaceutical composition for administration to a subject in need thereof. More specifically, the modified coagulation protein can be admixed with a carrier and formulated in a pharmaceutical composition. As used herein, a carrier or "pharmaceutically acceptable carrier" is a pharmaceutically acceptable solvent, suspending agent or any other pharmacologically inert vehicle for delivering one or more active compounds to the subject, and is typically liquid or solid. A pharmaceutical carrier is generally selected to provide the desired property (bulk, consistency, etc.), when combined with components of a given pharmaceutical composition, in view of the intended administration mode. Typical pharmaceutical carriers include, but are not limited to binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycotate, etc.); and wetting agents (e.g., sodium lauryl sulphate, etc.).

Modified coagulation proteins disclosed here may be administered with a pharmaceutically-acceptable diluent, carrier, or excipient, in unit dosage form. Conventional pharmaceutical practice may be employed to provide suitable formulations or compositions to administer such compositions to subjects. Although intravenous administration is preferred, any appropriate route of administration may be employed, for example, oral, perenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. Therapeutic formulations may be in the form of liquid solutions or suspension for intravenous administration; in the form of tablets or capsules for oral administration, formulations; and in the form of powders, nasal drops, or aerosols for intranasal formulations.

Methods well known in the art for making formulations are found in, for example, Remington: The Science and Practice of Pharmacy, (19$^{th}$ ed.) ed. A. R. Gennaro A R., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the disclosure include ethylenevinyl acetate copolymer particles, osmotic pumps, implantable infusion systems, and liposomes. Formulations for inhalation may contain excipients, (e.g. lactose) or may be aqueous solutions containing, for example, polyoxyethylene-9-lauryl ether, glycocholate and deoxycholate, or may be oily solutions for administration in the form of nasal drops, or as a gel.

In order to provide a therapeutic benefit, the modified coagulation protein is administered at a "pharmaceutically/therapeutically effective amount". The expressions "pharmaceutically effective amount" or "therapeutically effective amount" refers to an amount (dose) effective in treating a patient and/or alleviating its symptoms. It is also to be understood herein that a "pharmaceutically effective amount" of the modified coagulation protein can be interpreted as an amount giving a desired therapeutic effect, either taken in one dose or in any dosage or route, taken alone or in combination with other therapeutic agents.

A therapeutically effective amount or dosage of the modified coagulation protein disclosed herein or a pharmaceutical composition comprising the modified proteins, may range from about 0.001 to 30 mg/kg body weight, with other ranges of the disclosure including about 0.01 to 25 mg/kg body weight, about 0.025 to 10 mg/kg body weight, about 0.3 to 20 mg/kg body weight, about 0.1 to 20 mg/kg body weight, about 1 to 10 mg/kg body weight, 2 to 9 mg/kg body weight, 3 to 8 mg/kg body weight, 4 to 7 mg/kg body weight, 5 to 6 mg/kg body weight, and 20 to 50 mg/kg body weight. In other embodiments, a therapeutically effective amount or dosage may range from about 0.001 to 50 mg total, with other ranges of the disclosure including about 0.01 to 10 mg, about 0.3 to 3 mg, about 3 to 10 mg, about 6 mg, about 9 mg, about 10 to 20 mg, about 20-30 mg, about 30 to 40 mg, and about 40 to 50 mg.

As shown herein, the modified coagulation protein alone is shown to increase the thrombolytic and/or fibrinolytic activity of constitutive tPA. As such, in an embodiment, the modified coagulation protein can thus be used as a thrombolytic agent for dissolving a clot in vivo. In order to do so, a therapeutic dose of the modified coagulation protein is administered to a subject in need thereof (having a clot(s) and would benefit from reducing the size and/or number of clot(s)). The modified blood coagulation protein can be used alone, or in combination with another thrombolytic agent.

In an embodiment, the administration of the modified coagulation protein (or a pharmaceutical composition comprising such modified protein) can be used as an adjunct therapy to reduce the dose of a current thrombolytic agent, as shown here. Such agents include, but are not limited to, tPA, a tissue plasminogen activator variant (such as, for example, tenecteplase), urokinase and streptokinase. When used in combination with a modified coagulation protein, it is possible to administer a lower dose of a thrombolytic agent, even a dose to be considered sub-therapeutic (when administered in the absence of the modified coagulation protein). In an additional or optional embodiment, when used in combination with a modified coagulation protein, it may be possible to administer the thrombolytic agent at a time which is considered outside the effective window after the onset of symptoms (e.g. more than three hours after myocardial infarction or 5 hours after stroke) and still observe beneficial therapeutic effect in the subject.

As also shown herein, the modified coagulation protein is able to reduce the formation of a clot (anticoagulation activity). As such, in yet another embodiment, the modified coagulation protein can be used as an anticoagulant for reducing the formation of a clot in vivo. In order to do so, a therapeutic dose of the modified coagulation protein (which can optionally be formulated in a pharmaceutical composition) is administered to a subject in need thereof (having a clot(s) and could benefit from reducing the formation of the clot(s)). The modified coagulation protein can be used alone or in combination with another anticoagulant, such as, for example, heparin or its derivatives.

The present invention will be more readily understood by referring to the following examples which are given to illustrate the invention rather than to limit its scope.

Example I

Synthesis of Xa-K

FXa was chemically modified into Xa-K, via a histidine residue located in its active site, to be linked to a C-terminal lysine (CTK) by a spacer. The addition of a CTK to a serine protease is a three step procedure. The first step involves producing the CTK-linked to a thiol-reactive spacer (e.g. Lys-mPEG$_4$). In this example, tetra ethylene glycol was used (PEG$_4$). The second part involves irreversibly adding a thiol to the active site of the protease. The third part is to combine the Lys-mPEG$_4$ and the thiol-modified protease.

Preparation of Lys-mPEG4.

To a solution of succinimidyl-([N-maleimidopropionamido]-ethyleneglycol$_4$) ester (smPeg4; 30 mg, 0.058 mmol, Thermo Scientific #22104) in dimethylformamide (0.2 ML) was added N-ε-tertiary-butoxycarbonyl-L-lysine (16 mg, 0.065 mmol, Novabiochem #8.54105.0005) followed by diisopropyl ethylamine (0.03 mL, 0.17 mmol). The reaction mixture was stirred at room temperature for 2 h. Diethyl ether (3 mL) was added and the resultant suspension was subjected to centrifugation to isolate a white precipitate. The solid was resuspended in dichloromethane (1 mL) and trifluoroacetic acid (0.5 mL) was added. The reaction mixture was stirred at room temperature for 1 h and then was concentrated. The crude oil was purified via preparative HPLC (Waters XBridge preparative C18 column) as a transparent film and subjected to MALDI-TOF mass spectrometry for identification and quality analysis.

Preparation of the SH-Labeled Protease.

Purified FXa in 5 mM MES, 0.3 M NaCl, 1 mM EDTA, pH 6.0 (a heterogeneous mixture of alpha and beta) at a final concentration of 46 µM, was combined with Na-[(acetyl-thio)acetyl]-D-Phe-Pro-Arg-CH$_2$Cl (ATA-FPRck; Innovative Research). The final concentration of ATA-FPRck was 350 µM and was added in three equal amounts allowing each to react for 5 minutes. FXa active site modification was confirmed by loss of activity measured by hydrolysis of the chromogenic substrate S2765 (Diapharma). The ATA-FPR- FXa was subject to buffer exchange into 10 mM HEPES, 0.3 M NaCl, 1 mM EDTA, pH 7.0 using a G25 desalting column or dialysis.

Final Xa-K Generation.

After measuring the protein concentration by absorption spectroscopy, ATA-FPR-FXa was adjusted to 14 µM and combined with 70 µM Lys-mPEG$_4$ in 0.1 M hydroxylamine in 10 mM HEPES, 0.3 M NaCl, 1 mM EDTA, pH 7.0. After incubation for 1 h at room temperature the Xa-K was dialyzed against 20 mM phosphate, 150 mM NaCl, pH 7.4. The resulting Xa-K (0.5 µL) did not induce clotting of re-calcified citrated plasma (data not shown). The final Xa-K ran at a slightly higher apparent molecular weight than the starting unmodified FXa on reducing sodium dodecyl sulphate polyacrylamide (%) electrophoresis. The Xa-K is stored at −80° C. without loss of plasma fibrinolytic activity for at least 6 months.

Example II

Biological Properties of Xa-K

Figure 2A:
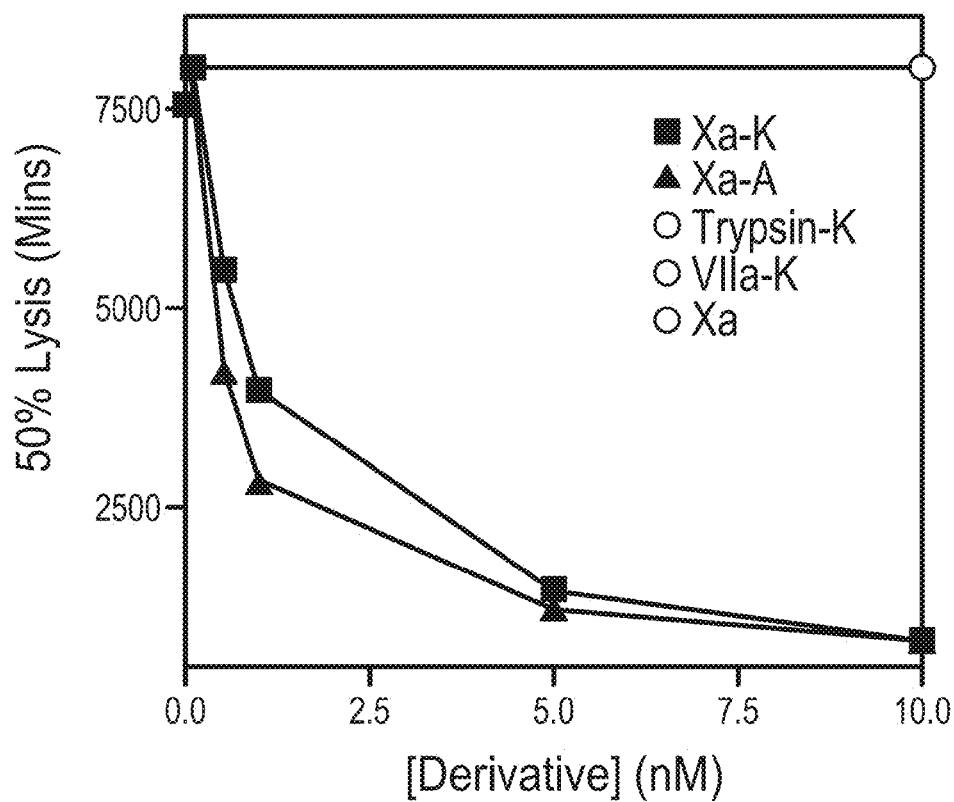
FIG. 2 illustrates that low levels of Xa-K enhance fibrinolysis. (A) Normal citrated plasma was supplemented with 25 pM tPA and clotting was induced with 15 mM $Ca^{2+}$ and 3 nM thrombin. Clot amount was followed by turbidity at $OD_{405nm}$ and the time to 50% lysis was determined at various concentrations of Xa-K or Xa-A. n=3±SD Results as shown as the time (in minutes) to achieve 50% lysis of the clot in function of Xa-K concentration (nM). (B) Under these conditions, unmodified FXa at 100 nM had no effect on plasma fibrinolysis, whereas thrombin that was modified identically to Xa-K (i.e. IIa-K) or FXa modified with a C-terminally tethered alanine (Xa-A) significantly decreased the time to complete fibrinolysis at a relatively high concentration of 100 nM; grey zones are standard deviation for time-course data, n=3.
Figure 2B:
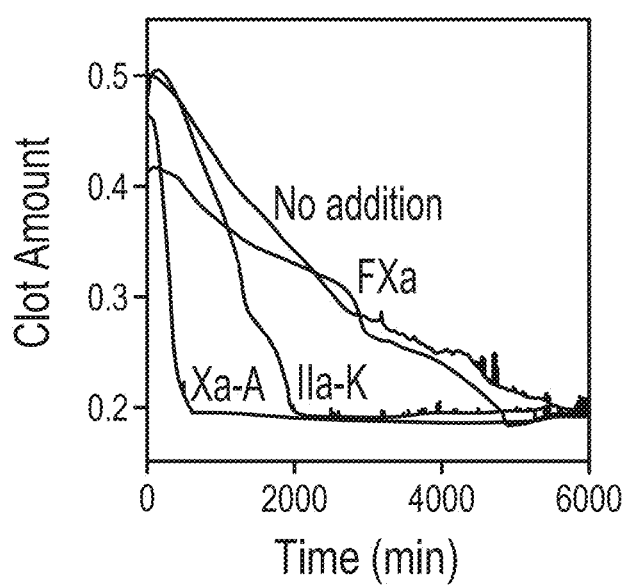

To test the in vitro function of Xa-K obtained in Example I, fibrinolysis of a clot formed in normal plasma was followed by turbidity (light scattering). Briefly, normal citrated plasma was supplemented with 25 pM tPA and clotting was induced with 15 mM Ca$^{2+}$ and 3 nM thrombin, according to a published method (Talbot et al. 2013). Clot amount was followed at OD$_{405nm}$. The time to achieve 50% lysis was determined at various concentrations of Xa-K. With no added Xa-K, the plasma clot very slowly dissolves over the course of ~7 days (FIG. 2A). As little as 0.25 nM Xa-K reduced the time to achieve 50% fibrinolysis of plasma by approximately 5-fold. When 1 nM was introduced into plasma, the time to dissolve the clot was accelerated by nearly 10-fold (FIG. 2A). At 10 nM concentrations of identically CTK-modified factor VIIa (referred to as VIIa-K) or trypsin (referred to as trypsin-K), or 100 nM unmodified FXa (FIG. 2A, open symbol) no effect of plasma fibrinolysis was observed under these conditions. However, at 100 nm, IIa-K some fibrinolytic activity in plasma was demonstrated (FIG. 2B). FIG. 2A also demonstrates that incorporation of PEG-tethered Ala into the active site of FXa very effectively reduces the time to reach 50% plasma clot lysis. FIG. 2B shows examples of the full plasma clot fibrinolysis profiles comparing Xa-A, IIa-K, unmodified FXa and no addition.

Figure 3A:
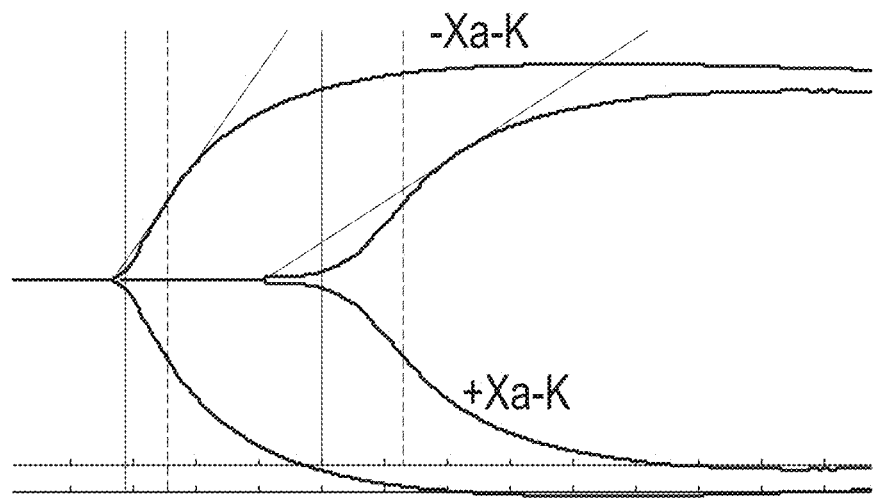
FIG. 3 illustrates that Xa-K inhibits coagulation. Whole blood was recalcified (11 mM) in the presence or absence of Xa-K (10 nM) and coagulation parameters were followed by thromboelastography (TEG). (A) Thromboelastography results shown that when Xa-K is present, the time to clot lysis is decreased. The time until first evidence of clot formation (R), the time from R until a 20 mm clot is formed (K) and the tangent of the curve at K indicating the rate of clot formation (angle) are presented in Table 1. (B) First derivative of FIG. 3A showing that Xa-K increases the maximum lysis rate. (C) Differentiation of 180 minute TEG tracings was done using GraphPad Prism 4 software. The peak values during clot dissolution were plotted.
Figure 3B:
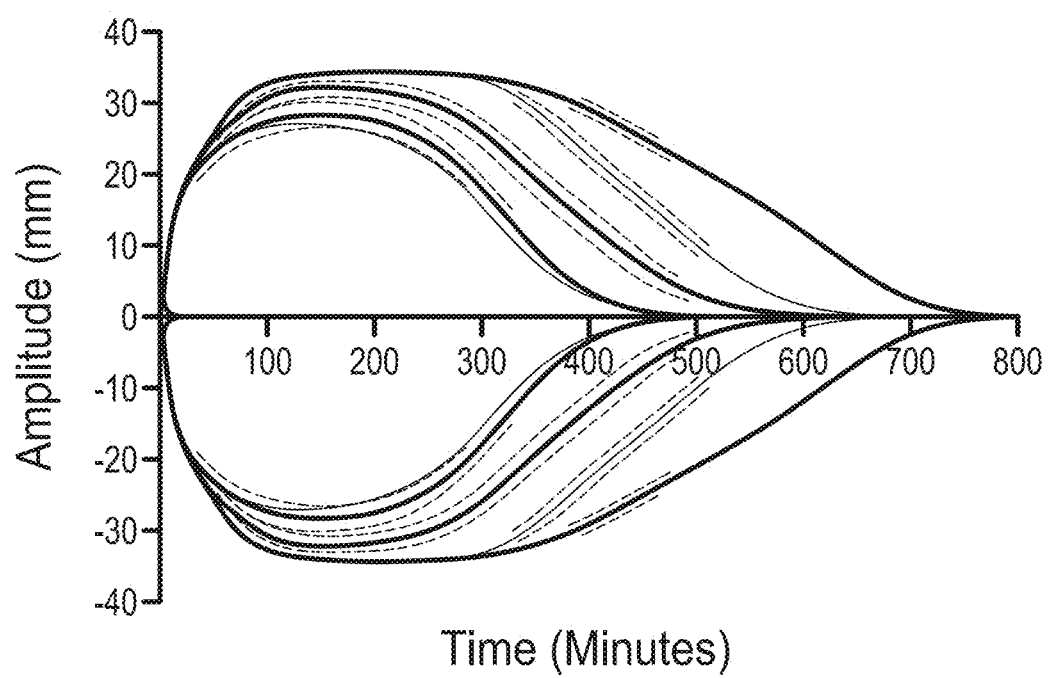
Figure 3C:
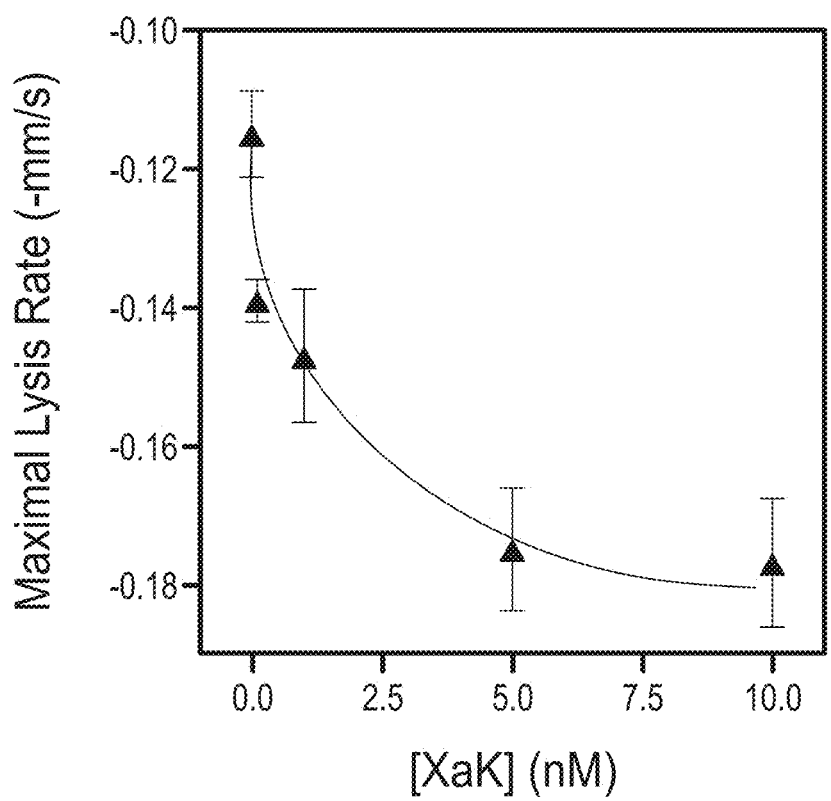

The anticoagulant properties of Xa-K are demonstrated in FIGS. 3A to 3C, where citrated whole blood was induced to clot by recalcification in the presence or absence of Xa-K and followed by thromboelastography according to manufacturer's instructions. Modifying the serine protease active site of FXa has been shown previously to act as a competitive inhibitor of the complex that is responsible for generating thrombin (FXa-FVa-proPL; i.e prothrombinase) (U.S. Pat. Nos. 5,583,107; 5,635,481; 5,650,314 and 5,795,863). It was observed that the time to first observe clot formation was prolonged from ~10 to ~25 seconds by addition of 10 nM Xa-K as measured by this method. The time until first evidence of clot formation (R), the time from R until a 20 mm clot is formed (K) and the tangent of the curve at K indicating the rate of clot formation (angle) derived from the thromboelastography results are presented in Table 1.

TABLE 1

The time until first evidence of clot formation (R), the time from R until a 20 mm clot is formed (K) and the tangent of the curve at K indicating the rate of clot formation (angle) of the thromboelastography results extrapolated from FIG. 3A.

|  | R (min) | K (min) | Angle (degrees) |
| --- | --- | --- | --- |
| In the absence of Xa-K | 9.3 | 3.2 | 50.2 |
| In the presence of Xa-K | 25.0 | 6.4 | 28.6 |

Figure 4:
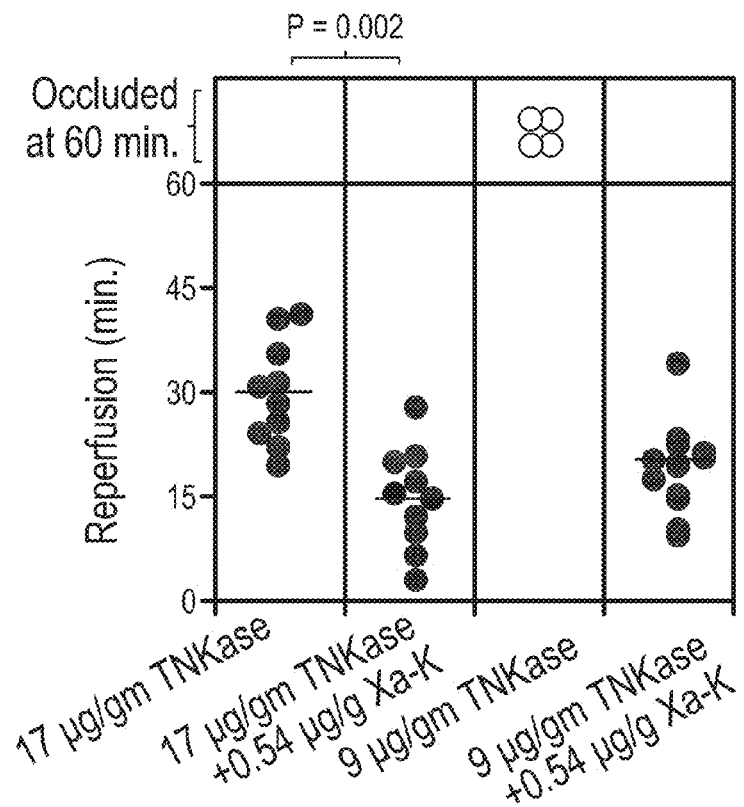
FIG. 4 illustrates that Xa-K enhances therapeutic and sub-therapeutic doses of tenecteplase in a carotid occlusion model. A thrombus was induced in exposed carotid arteries of CD1 mice and an ultrasound probe was installed to measure blood flow. The tPA variant, tenecteplase (TNKase) was injected into the tail vein at a therapeutic and sub-therapeutic dose, with or without Xa-K. The time to reach complete reperfusion is indicated for each mouse. The experimental end-point was 60 minutes. Bars indicate average. •: complete reperfusion at 60 minutes; ○: completely occluded at 60 minutes.

To test some of the in vivo properties of Xa-K in a large vessel model of thrombolysis, a thrombus was induced (with ferric chloride) in murine carotid arteries and reperfusion monitored by ultrasound, according to a published method (Sheffield et al., 2012). Briefly, a thrombus was induced in the surgically exposed carotid artery of CD1 mice and a Doppler ultrasound cuff was installed to measure blood flow. The tPA variant, tenecteplase (TNKase; 17 µg/g mouse) was injected in the tail with or without Xa-K (0.54 µg/g/mouse). As shown in FIG. 4, the addition of ~10% the molar ratio of Xa-K to a therapeutic dose of the tPA analogue, TNKase, decreased the time to reperfusion by half. These results suggest that the dose of TNKase may be further decreased as the enzyme and cofactor function at a 1:1 molar ratio. Thus, reducing the TNKase to a sub-therapeutic dose (9 µg/g) alone, it was observed that reperfusion was still facilitated in the presence of Xa-K at an indistinguishable time compared to the higher dose of TNKase. These data show that the TNKase dose can be reduced using Xa-K as a cofactor adjunct.

Figure 5:
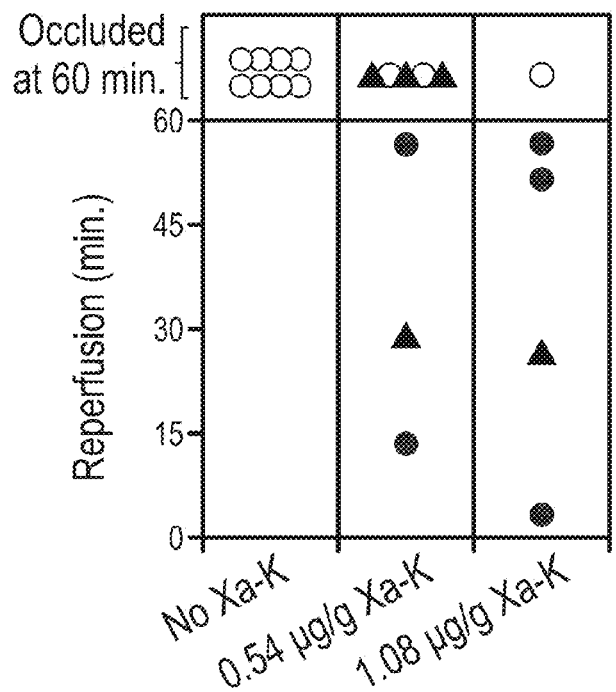
FIG. 5 illustrates that Xa-K alone restores blood flow in a carotid occlusion model. Methodology used is the same as in FIG. 4, except that no tenecteplase was used. Xa-K alone was injected in the CD1 mice tail vein at two concentrations. Results are shown as time from treatment to reach reperfusion (min). The proportion of mice achieving restored blood flow was dependent on the concentration of Xa-K. The experimental end-point was 60 minutes. •: complete reperfusion at 60 minutes; ○: completely occluded (no reperfusion) at 60 minutes; ▲: partial reperfusion at experimental end-point.

In addition to evaluating the adjunctive thrombolytic activity of Xa-K, experiments were conducted to determine if Xa-K alone can enhance the tPA activity intrinsic to the mouse. The carotid of eight control mice receiving saline remained completely occluded up to the end of the experiment at 60 minutes (FIG. 5). In contrast, animals that received Xa-K alone at either 0.54 µg/g or 1.08 µg/g had examples of reperfusion. Of the eight mice receiving the lower dose, by 60 minutes, complete carotid reperfusion was achieved for two and incompletely for one. An additional three mice achieved partial reperfusion, but re-occluded by 60 minutes. At the higher dose of Xa-K, blood flow was completely or partially restored in 80% of carotids by the end of the 60 minute experiment, demonstrating a direct effect on endogenous tPA and dose dependence on Xa-K.

Figure 6:
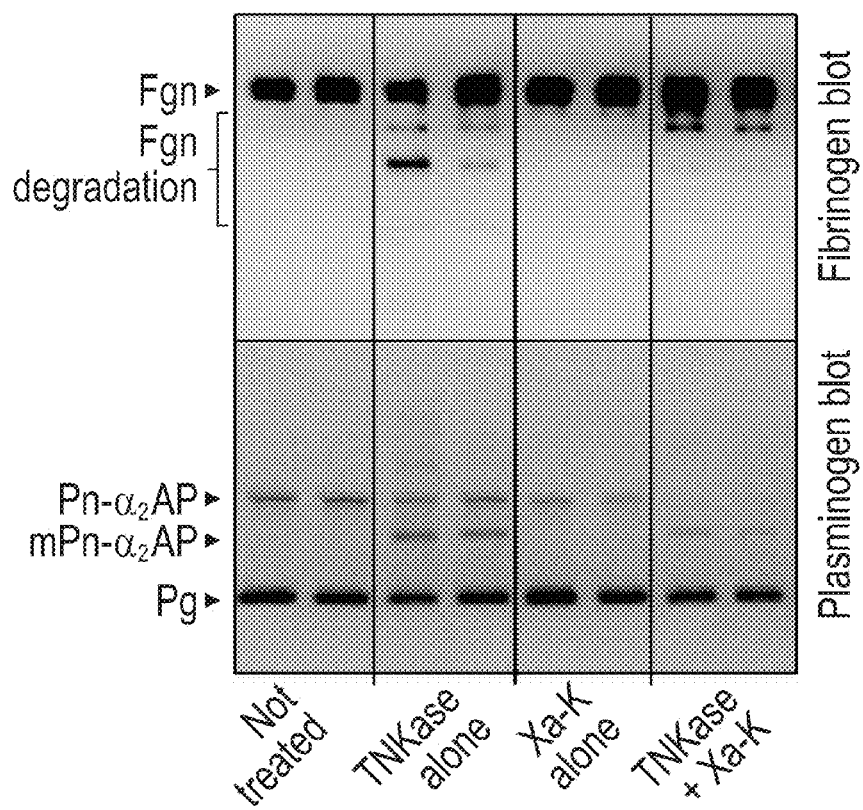
FIG. 6 illustrates that Xa-K does not induce systemic fibrinolysis. At the close of in vivo experiments (FIGS. 4 and 5) citrated plasma was prepared from blood obtained by cardiac puncture. Two samples were analyzed for each of: no TNKase or Xa-K (reperfusion did not occur, FIG. 4); 17 µg/gm TNKase (samples near the average reperfusion time, FIG. 4); 0.54 µg/gm Xa-K (the two samples that induced reperfusion, FIG. 5); and 17 µg/gm TNKase+0.54 µg/gm Xa-K (samples near the average reperfusion time, FIG. 4). In addition to having no discernible systemic effects alone, Xa-K attenuates the systemic effects of TNKase. Top blots (non-reduced SDS-PAGE) are fibrinogen blots, whereas lower blots (non-reduced SDS-PAGE) are plasminogen blots. Pn, plasmin; mPn, mini-plasmin; $\alpha_2AP$, alpha-2-antiplasmin; min-$\alpha_2AP$, mini-alpha-2-antiplasmin; Fgn, fibrinogen.
Figure 7A:
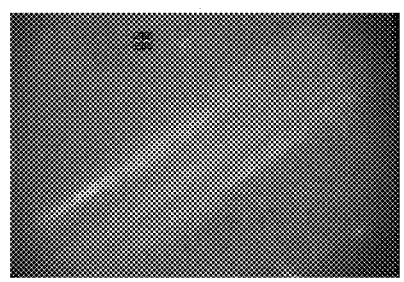
FIG. 7 illustrates that Xa-K alone inhibits occlusion in a mesenteric arteriole thrombosis model. Representative intravital micrographs are provided for control mouse not induced to form a thrombus (A), mouse induced to form a thrombus and remaining untreated (B), treated with 0.9 µg/gm tPA (C) or with 0.54 µg/gm Xa-K (D). Micrographs were taken 10 minutes post-thrombus induction.
Figure 7C:
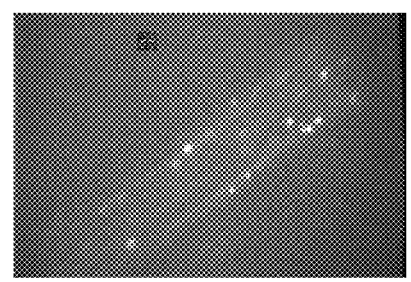
Figure 7B:
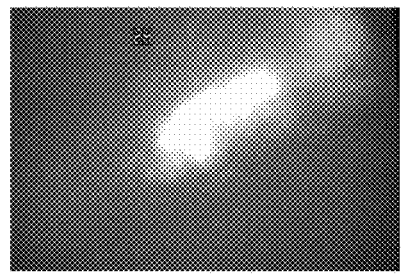
Figure 7D:
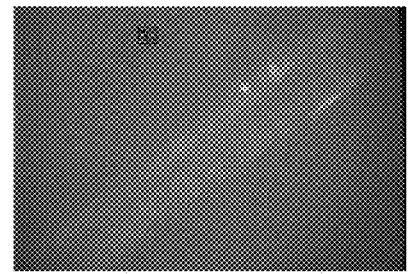

Although Xa-K binds procoagulant phospholipid (proPL) and is expected to confer consequential clot-localized thrombolysis in vivo, mouse plasma was evaluated for evidence of systemic fibrinolysis. Compared to occluded mice not subjected to thrombolytic treatment (FIG. 6), TNKase alone induced systemic fibrin(ogen) and plasminogen degradation. In contrast, plasma from the two mice whose blood flow was restored completely after treatment with Xa-K alone (FIG. 5; 0.54 µg/g) showed insignificant systemic activation of fibrinolysis compared to untreated mice. Likely due to localization by Xa-K, the systemic effect of TNKase alone was furthermore attenuated when TNKase was combined with Xa-K.

To test the efficacy of Xa-K in a model of small vessel occlusion, intravital microscopy was conducted. Briefly, fluorescent platelets were followed in mesenteric arterioles of Balb/c mice by intravital microscopy (Ni et al., 2001). Thrombus formation was either not induced or induced by ferric chloride. Induced mice were either left untreated or treated with 0.9 µg/g of human tPA or 0.54 µg/g of human Xa-K. As shown in FIG. 7, Xa-K alone functions at least as well as tPA. Unlike the carotid model, where just the thrombolytic effect of Xa-K was evaluated, both the thrombolytic and anticoagulant functions of Xa-K were simultaneously acting in this experiment.

Figure 8:
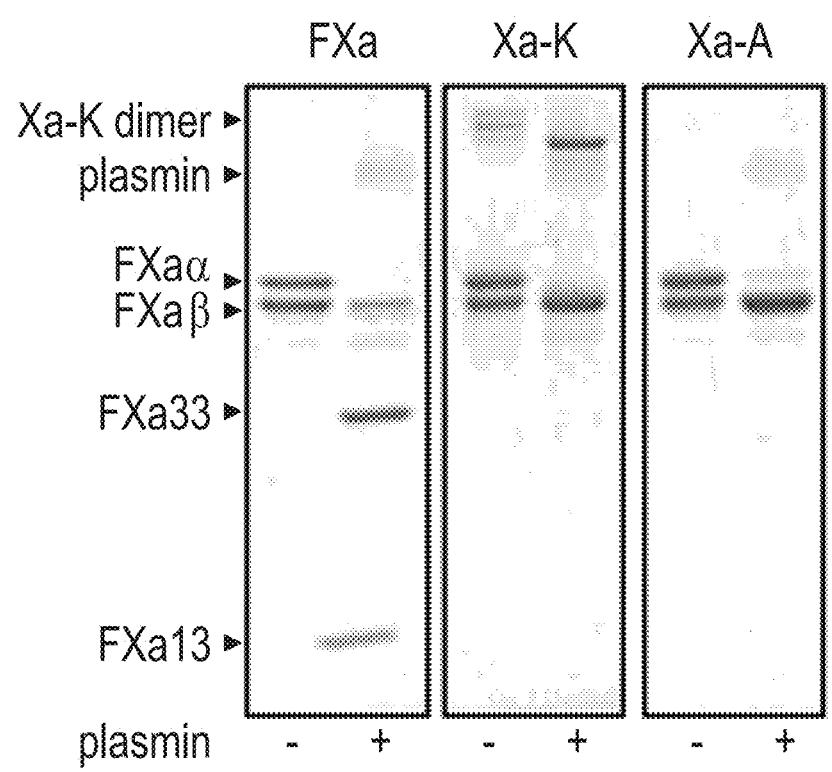
FIG. 8 illustrates that Xa-K and Xa-A (i.e. Xa with a C-terminal alanine residue) are protected from cleavage by plasmin to the Xa33/13 fragments. Purified FXaαβ, Xa-K or Xa-A (5 µM) were treated with or without plasmin (0.1 µM), in the presence of 5 mM CaCl2 and 50 µM 25% phosphatidyl serine/75% phosphatidyl choline small unilamellar vesicles for 20 min. at room temperature and run on SDS-PAGE (10% acrylamide) under non-reducing conditions. Left blot represents results obtained with FXaαβ, middle blot with Xa-K and left blot with Xa-A.

While addition of a CTK to the active site of FXa to produce Xa-K is anticipated to be an important aspect of its biological activity in fibrinolysis, it is also anticipated that preventing conversion to a previously described plasmin-mediated fragment of FXa, Xa33/13, is also important. In a purified fibrinolysis experiment Xa33/13 has activity that is nearly comparable to FXa (Talbot et al., 2010). However, the conversion of FXa to Xa33/13 in plasma is believed to rapidly facilitate the inhibition of its tPA accelerating function. Therefore, the cleavage of FXa and Xa-K by plasmin were compared. FIG. 8 shows that modification of FXa to form Xa-K limits Xa33/13 production by plasmin.

While the invention has been described in connection with specific embodiments thereof, it will be understood that the scope of the claims should not be limited by the preferred embodiments set forth in the examples, but should be given the broadest interpretation consistent with the description as a whole.

REFERENCES

Ni H, Ramakrishnan V, Ruggeri Z M, Papalia J M, Phillips D R, Wagner D D. Increased thrombogenesis and embolus formation in mice lacking glycoprotein V. Blood. 2001 Jul. 15; 98(2):368-73.

Pryzdial E L, Kessler G E. Autoproteolysis or plasmin-mediated cleavage of factor Xaalpha exposes a plasminogen binding site and inhibits coagulation. J Biol Chem. 1996 Jul. 12; 271(28):16614-20.

Sheffield W P, Eltringham-Smith L J, Bhakta V, Gataiance S. (2012) Reduction of thrombus size in murine models of thrombosis following administration of recombinant alpha-1-proteinase inhibitor mutant proteins. Thromb Haemost 107:972-84.

Talbot K, Meixner S C, Pryzdial E L G. Enhanced fibrinolysis by proteolysed coagulation FXa. (2010) Biochem Biophys Acta 1804:723-30.

Talbot, K., Meixner, S. C. and Pryzdial, E. L. G. (2013) Proteolytic Modulation of FXa-Antithrombin Complex Enhances Fibrinolysis in Plasma. Biochimica et Biophysica Acta doi: 10.1016/j.bbapap.2013.02.007

What is claimed is:

1. An isolated and modified blood coagulation protein, said blood coagulation protein being from the vitamin K-dependent family and having a modified histidine (His) or serine (Ser) residue of the following formula:

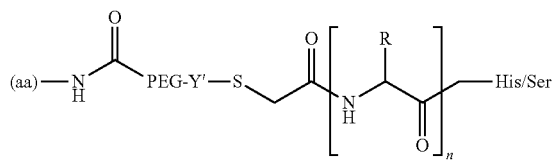

wherein:
(aa) is lysine or alanine,
PEG is 2-8 linear repeating units having the following formula

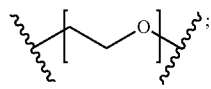

where each carbon atom of said unit is optionally substituted,

His/Ser is a histidine residue or a serine residue of the blood coagulation protein located within a serine protease active site, said His/Ser is covalently linked to the CH$_2$ moiety by the catalytic site imidazole-nitrogen atom of said histidine or hydroxyl of said serine;

R is H or a residue of a natural or non-natural amino acid,
n is an integer ranging from 2 to 4;
and Y' is

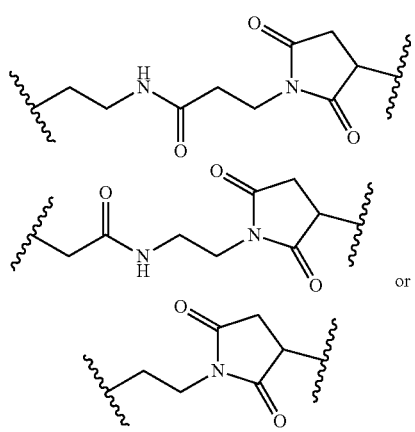

wherein the blood coagulation protein is further defined as Factor Xa or Factor IIa.

2. The isolated and modified blood coagulation protein of claim 1, wherein the blood coagulation protein is a human protein.

3. The isolated and modified blood coagulation protein of claim 1, wherein the blood coagulation protein is isolated from blood or a blood derivative.

4. The isolated modified blood coagulation protein of claim 1, wherein the blood coagulation protein is a Factor Xa (FXa) protein.

5. The isolated and modified blood coagulation protein of claim 4, wherein the FXa protein has (i) a light chain having an amino acid sequence as set forth at positions between 41 to 179 of SEQ ID NO:1 or 2 and (ii) a heavy chain having an amino acid sequence as set forth at positions between 235 to 467, between 235 to 469, between 235 to 473, between 235 to 475, between 235 to 487, or between 235 to 488 of SEQ ID NO: 1 or 2.

6. A combination of a plurality of isolated and modified blood coagulation protein as defined in claim 5 comprising:
at least one isolated and modified FXa having, as a heavy chain, an amino acid sequence as set forth at positions between 235 to 487 or between 235 to 488 of SEQ ID NO: 1 or 2;
at least one isolated and modified FXa having, as a heavy chain, an amino acid sequence as set forth at positions between 235 to 467, between 235 to 473 or between 235 to 475 of SEQ ID NO: 1 or 2; and
at least one isolated and modified FXa having, as a heavy chain, an amino acid sequence as set forth at positions between 235 to 469 of SEQ ID NO: 1 or 2.

7. A method for dissolving a clot in a subject in need thereof, said method comprising administering a therapeutic effective amount of the isolated modified blood coagulation protein of claim 1 to the subject so as to dissolve the clot.

8. A method of improving the therapeutic property of a thrombolytic agent in a subject in need thereof, said method comprising administering a therapeutic effective amount of the isolated modified blood coagulation protein of claim 1 with the thrombolytic agent to the subject.

9. The method of claim 8, wherein the thrombolytic agent is administered at a dose considered sub-therapeutic when used in the absence of the pharmaceutical composition.

10. The method of claim 8, wherein the thrombolytic agent is administered at a timing considered sub-therapeutic when used in the absence of the pharmaceutical composition.

11. The method of claim 8, wherein the thrombolytic agent is selected from the group consisting of tissue plasminogen activator, a modified tissue plasminogen activator, urokinase and streptokinase.

12. The method of claim 11, wherein the modified tissue plasminogen activator is tenecteplase.

13. The isolated and modified blood coagulation protein of claim 1, wherein the (aa) is a natural amino acid.

14. The isolated and modified blood coagulation protein of claim 1, wherein the (aa) is lysine.

15. The isolated and modified blood coagulation protein of claim 1, wherein the (aa) is alanine.

16. The isolated and modified blood coagulation protein of claim 1, wherein the PEG is —(CH$_2$—CH$_2$—O—)$_{2-8}$.

17. The isolated and modified blood coagulation protein of claim 16, wherein the PEG is —(CH$_2$—CH$_2$—O—)$_{4-8}$.

18. The isolated and modified blood coagulation protein of claim 16, wherein the PEG is —(CH$_2$—CH$_2$—O—)$_4$.

19. The isolated modified blood coagulation protein of claim 1, wherein the blood coagulation protein is a Factor IIa (FIIa) protein.

\* \* \* \* \*

SEQUENCE LISTING

```
<160> NUMBER OF SEQ ID NOS: 4

<210> SEQ ID NO 1
<211> LENGTH: 488
<212> TYPE: PRT
<213> ORGANISM: Homo sapiens
<220> FEATURE:
<221> NAME/KEY: VARIANT
<222> LOCATION: (7)..(7)
<223> OTHER INFORMATION: Isoleucine
<220> FEATURE:
<221> NAME/KEY: VARIANT
<222> LOCATION: (30)..(30)
<223> OTHER INFORMATION: Histidine
<220> FEATURE:
<221> NAME/KEY: MOD_RES
<222> LOCATION: (46)..(46)
<223> OTHER INFORMATION: 4-carboxyglutamate
<220> FEATURE:
<221> NAME/KEY: VARIANT
<222> LOCATION: (47)..(47)
<223> OTHER INFORMATION: Glycine
<220> FEATURE:
<221> NAME/KEY: MOD_RES
<222> LOCATION: (47)..(47)
<223> OTHER INFORMATION: 4-carboxyglutamate
<220> FEATURE:
<221> NAME/KEY: VARIANT
<222> LOCATION: (51)..(51)
<223> OTHER INFORMATION: Valine
<220> FEATURE:
<221> NAME/KEY: VARIANT
<222> LOCATION: (54)..(54)
<223> OTHER INFORMATION: Glycine or Lysine
<220> FEATURE:
<221> NAME/KEY: MOD_RES
<222> LOCATION: (54)..(54)
<223> OTHER INFORMATION: 4-carboxyglutamate
<220> FEATURE:
<221> NAME/KEY: MOD_RES
<222> LOCATION: (56)..(56)
<223> OTHER INFORMATION: 4-carboxyglutamate
<220> FEATURE:
<221> NAME/KEY: MOD_RES
<222> LOCATION: (59)..(59)
<223> OTHER INFORMATION: 4-carboxyglutamate
<220> FEATURE:
<221> NAME/KEY: MOD_RES
<222> LOCATION: (60)..(60)
<223> OTHER INFORMATION: 4-carboxyglutamate
```

-continued

```
<220> FEATURE:
<221> NAME/KEY: MOD_RES
<222> LOCATION: (65)..(65)
<223> OTHER INFORMATION: 4-carboxyglutamate
<220> FEATURE:
<221> NAME/KEY: MOD_RES
<222> LOCATION: (66)..(66)
<223> OTHER INFORMATION: 4-carboxyglutamate
<220> FEATURE:
<221> NAME/KEY: MOD_RES
<222> LOCATION: (69)..(69)
<223> OTHER INFORMATION: 4-carboxyglutamate
<220> FEATURE:
<221> NAME/KEY: VARIANT
<222> LOCATION: (72)..(72)
<223> OTHER INFORMATION: Glutamine
<220> FEATURE:
<221> NAME/KEY: MOD_RES
<222> LOCATION: (72)..(72)
<223> OTHER INFORMATION: 4-carboxyglutamate
<220> FEATURE:
<221> NAME/KEY: MOD_RES
<222> LOCATION: (79)..(79)
<223> OTHER INFORMATION: 4-carboxyglutamate
<220> FEATURE:
<221> NAME/KEY: VARIANT
<222> LOCATION: (91)..(91)
<223> OTHER INFORMATION: Lysine
<220> FEATURE:
<221> NAME/KEY: MOD_RES
<222> LOCATION: (103)..(103)
<223> OTHER INFORMATION: 3-hydroxyaspartate
<220> FEATURE:
<221> NAME/KEY: VARIANT
<222> LOCATION: (142)..(142)
<223> OTHER INFORMATION: Lysine
<220> FEATURE:
<221> NAME/KEY: VARIANT
<222> LOCATION: (149)..(149)
<223> OTHER INFORMATION: Tyrosine
<220> FEATURE:
<221> NAME/KEY: VARIANT
<222> LOCATION: (151)..(151)
<223> OTHER INFORMATION: Tyrosine
<220> FEATURE:
<221> NAME/KEY: VARIANT
<222> LOCATION: (152)..(152)
<223> OTHER INFORMATION: Threonine
<220> FEATURE:
<221> NAME/KEY: VARIANT
<222> LOCATION: (192)..(192)
<223> OTHER INFORMATION: Arginine
<220> FEATURE:
<221> NAME/KEY: VARIANT
<222> LOCATION: (289)..(289)
<223> OTHER INFORMATION: Arginine
<220> FEATURE:
<221> NAME/KEY: VARIANT
<222> LOCATION: (304)..(304)
<223> OTHER INFORMATION: Lysine
<220> FEATURE:
<221> NAME/KEY: VARIANT
<222> LOCATION: (322)..(322)
<223> OTHER INFORMATION: Asparagine
<220> FEATURE:
<221> NAME/KEY: VARIANT
<222> LOCATION: (327)..(327)
<223> OTHER INFORMATION: Tryptophan
<220> FEATURE:
<221> NAME/KEY: VARIANT
<222> LOCATION: (338)..(338)
<223> OTHER INFORMATION: Methionine
<220> FEATURE:
<221> NAME/KEY: VARIANT
<222> LOCATION: (350)..(350)
<223> OTHER INFORMATION: Lysine
<220> FEATURE:
<221> NAME/KEY: VARIANT
<222> LOCATION: (358)..(358)
```

```
<223> OTHER INFORMATION: Methionine
<220> FEATURE:
<221> NAME/KEY: VARIANT
<222> LOCATION: (363)..(363)
<223> OTHER INFORMATION: Serine
<220> FEATURE:
<221> NAME/KEY: VARIANT
<222> LOCATION: (366)..(366)
<223> OTHER INFORMATION: Cysteine
<220> FEATURE:
<221> NAME/KEY: VARIANT
<222> LOCATION: (374)..(374)
<223> OTHER INFORMATION: Proline
<220> FEATURE:
<221> NAME/KEY: VARIANT
<222> LOCATION: (383)..(383)
<223> OTHER INFORMATION: Serine
<220> FEATURE:
<221> NAME/KEY: VARIANT
<222> LOCATION: (390)..(390)
<223> OTHER INFORMATION: Phenylalanine
<220> FEATURE:
<221> NAME/KEY: VARIANT
<222> LOCATION: (404)..(404)
<223> OTHER INFORMATION: Arginine
<220> FEATURE:
<221> NAME/KEY: VARIANT
<222> LOCATION: (406)..(406)
<223> OTHER INFORMATION: Serine
<220> FEATURE:
<221> NAME/KEY: VARIANT
<222> LOCATION: (420)..(420)
<223> OTHER INFORMATION: Arginine
<220> FEATURE:
<221> NAME/KEY: VARIANT
<222> LOCATION: (448)..(448)
<223> OTHER INFORMATION: Asparagine

<400> SEQUENCE: 1

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205
```

-continued

```
Asp Pro Thr Glu Asn Pro Phe Asp Leu Leu Asp Phe Asn Gln Thr Gln
    210                 215                 220
Pro Glu Arg Gly Asp Asn Asn Leu Thr Arg Ile Val Gly Gly Gln Glu
225                 230                 235                 240
Cys Lys Asp Gly Glu Cys Pro Trp Gln Ala Leu Leu Ile Asn Glu Glu
                245                 250                 255
Asn Glu Gly Phe Cys Gly Gly Thr Ile Leu Ser Glu Phe Tyr Ile Leu
            260                 265                 270
Thr Ala Ala His Cys Leu Tyr Gln Ala Lys Arg Phe Lys Val Arg Val
        275                 280                 285
Gly Asp Arg Asn Thr Glu Gln Glu Glu Gly Gly Glu Ala Val His Glu
    290                 295                 300
Val Glu Val Val Ile Lys His Asn Arg Phe Thr Lys Glu Thr Tyr Asp
305                 310                 315                 320
Phe Asp Ile Ala Val Leu Arg Leu Lys Thr Pro Ile Thr Phe Arg Met
                325                 330                 335
Asn Val Ala Pro Ala Cys Leu Pro Glu Arg Asp Trp Ala Glu Ser Thr
            340                 345                 350
Leu Met Thr Gln Lys Thr Gly Ile Val Ser Gly Phe Gly Arg Thr His
        355                 360                 365
Glu Lys Gly Arg Gln Ser Thr Arg Leu Lys Met Leu Glu Val Pro Tyr
    370                 375                 380
Val Asp Arg Asn Ser Cys Lys Leu Ser Ser Ser Phe Ile Ile Thr Gln
385                 390                 395                 400
Asn Met Phe Cys Ala Gly Tyr Asp Thr Lys Gln Glu Asp Ala Cys Gln
                405                 410                 415
Gly Asp Ser Gly Gly Pro His Val Thr Arg Phe Lys Asp Thr Tyr Phe
            420                 425                 430
Val Thr Gly Ile Val Ser Trp Gly Glu Gly Cys Ala Arg Lys Gly Lys
        435                 440                 445
Tyr Gly Ile Tyr Thr Lys Val Thr Ala Phe Leu Lys Trp Ile Asp Arg
    450                 455                 460
Ser Met Lys Thr Arg Gly Leu Pro Lys Ala Lys Ser His Ala Pro Glu
465                 470                 475                 480
Val Ile Thr Ser Ser Pro Leu Lys
                485
```

<210> SEQ ID NO 2
<211> LENGTH: 488
<212> TYPE: PRT
<213> ORGANISM: Homo sapiens

<400> SEQUENCE: 2

```
Met Gly Arg Pro Leu His Leu Val Leu Leu Ser Ala Ser Leu Ala Gly
1               5                   10                  15
Leu Leu Leu Leu Gly Glu Ser Leu Phe Ile Arg Arg Glu Gln Ala Asn
            20                  25                  30
Asn Ile Leu Ala Arg Val Thr Arg Ala Asn Ser Phe Leu Glu Glu Met
        35                  40                  45
Lys Lys Gly His Leu Glu Arg Glu Cys Met Glu Glu Thr Cys Ser Tyr
    50                  55                  60
Glu Glu Ala Arg Glu Val Phe Glu Asp Ser Asp Lys Thr Asn Glu Phe
65                  70                  75                  80
Trp Asn Lys Tyr Lys Asp Gly Asp Gln Cys Glu Thr Ser Pro Cys Gln
                85                  90                  95
```

-continued

```
Asn Gln Gly Lys Cys Lys Asp Gly Leu Gly Glu Tyr Thr Cys Thr Cys
            100                 105                 110
Leu Glu Gly Phe Glu Gly Lys Asn Cys Glu Leu Phe Thr Arg Lys Leu
        115                 120                 125
Cys Ser Leu Asp Asn Gly Asp Cys Asp Gln Phe Cys His Glu Glu Gln
    130                 135                 140
Asn Ser Val Val Cys Ser Cys Ala Arg Gly Tyr Thr Leu Ala Asp Asn
145                 150                 155                 160
Gly Lys Ala Cys Ile Pro Thr Gly Pro Tyr Pro Cys Gly Lys Gln Thr
                165                 170                 175
Leu Glu Arg Arg Lys Arg Ser Val Ala Gln Ala Thr Ser Ser Ser Gly
            180                 185                 190
Glu Ala Pro Asp Ser Ile Thr Trp Lys Pro Tyr Asp Ala Ala Asp Leu
        195                 200                 205
Asp Pro Thr Glu Asn Pro Phe Asp Leu Leu Asp Phe Asn Gln Thr Gln
    210                 215                 220
Pro Glu Arg Gly Asp Asn Asn Leu Thr Arg Ile Val Gly Gly Gln Glu
225                 230                 235                 240
Cys Lys Asp Gly Glu Cys Pro Trp Gln Ala Leu Leu Ile Asn Glu Glu
                245                 250                 255
Asn Glu Gly Phe Cys Gly Gly Thr Ile Leu Ser Glu Phe Tyr Ile Leu
            260                 265                 270
Thr Ala Ala His Cys Leu Tyr Gln Ala Lys Arg Phe Lys Val Arg Val
        275                 280                 285
Gly Asp Arg Asn Thr Glu Gln Glu Glu Gly Gly Glu Ala Val His Glu
    290                 295                 300
Val Glu Val Val Ile Lys His Asn Arg Phe Thr Lys Glu Thr Tyr Asp
305                 310                 315                 320
Phe Asp Ile Ala Val Leu Arg Leu Lys Thr Pro Ile Thr Phe Arg Met
                325                 330                 335
Asn Val Ala Pro Ala Cys Leu Pro Glu Arg Asp Trp Ala Glu Ser Thr
            340                 345                 350
Leu Met Thr Gln Lys Thr Gly Ile Val Ser Gly Phe Gly Arg Thr His
        355                 360                 365
Glu Lys Gly Arg Gln Ser Thr Arg Leu Lys Met Leu Glu Val Pro Tyr
    370                 375                 380
Val Asp Arg Asn Ser Cys Lys Leu Ser Ser Ser Phe Ile Ile Thr Gln
385                 390                 395                 400
Asn Met Phe Cys Ala Gly Tyr Asp Thr Lys Gln Glu Asp Ala Cys Gln
                405                 410                 415
Gly Asp Ser Gly Gly Pro His Val Thr Arg Phe Lys Asp Thr Tyr Phe
            420                 425                 430
Val Thr Gly Ile Val Ser Trp Gly Glu Gly Cys Ala Arg Lys Gly Lys
        435                 440                 445
Tyr Gly Ile Tyr Thr Lys Val Thr Ala Phe Leu Lys Trp Ile Asp Arg
    450                 455                 460
Ser Met Lys Thr Arg Gly Leu Pro Lys Ala Lys Ser His Ala Pro Glu
465                 470                 475                 480
Val Ile Thr Ser Ser Pro Leu Lys
                485

<210> SEQ ID NO 3
<211> LENGTH: 481
```

```
<212> TYPE: PRT
<213> ORGANISM: Mus musculus
<220> FEATURE:
<221> NAME/KEY: MOD_RES
<222> LOCATION: (47)..(47)
<223> OTHER INFORMATION: 4-carboxyglutamate
<220> FEATURE:
<221> NAME/KEY: MOD_RES
<222> LOCATION: (54)..(54)
<223> OTHER INFORMATION: 4-carboxyglutamate
<220> FEATURE:
<221> NAME/KEY: MOD_RES
<222> LOCATION: (56)..(56)
<223> OTHER INFORMATION: 4-carboxyglutamate
<220> FEATURE:
<221> NAME/KEY: MOD_RES
<222> LOCATION: (59)..(59)
<223> OTHER INFORMATION: 4-carboxyglutamate
<220> FEATURE:
<221> NAME/KEY: MOD_RES
<222> LOCATION: (60)..(60)
<223> OTHER INFORMATION: 4-carboxyglutamate
<220> FEATURE:
<221> NAME/KEY: MOD_RES
<222> LOCATION: (65)..(65)
<223> OTHER INFORMATION: 4-carboxyglutamate
<220> FEATURE:
<221> NAME/KEY: MOD_RES
<222> LOCATION: (66)..(66)
<223> OTHER INFORMATION: 4-carboxyglutamate
<220> FEATURE:
<221> NAME/KEY: MOD_RES
<222> LOCATION: (69)..(69)
<223> OTHER INFORMATION: 4-carboxyglutamate
<220> FEATURE:
<221> NAME/KEY: MOD_RES
<222> LOCATION: (72)..(72)
<223> OTHER INFORMATION: 4-carboxyglutamate
<220> FEATURE:
<221> NAME/KEY: MOD_RES
<222> LOCATION: (75)..(75)
<223> OTHER INFORMATION: 4-carboxyglutamate
<220> FEATURE:
<221> NAME/KEY: MOD_RES
<222> LOCATION: (79)..(79)
<223> OTHER INFORMATION: 4-carboxyglutamate
<220> FEATURE:
<221> NAME/KEY: MOD_RES
<222> LOCATION: (103)..(103)
<223> OTHER INFORMATION: 3-hydroxyaspartate

<400> SEQUENCE: 3

Met Gly Ser Pro Val Gln Leu Ser Leu Leu Cys Val Val Leu Ala Ser
1               5                   10                  15

Leu Leu Leu Pro Gly Lys Gly Val Phe Ile Asn Arg Glu Arg Ala Asn
            20                  25                  30

Asn Val Leu Ala Arg Thr Arg Arg Ala Asn Ser Phe Phe Glu Glu Phe
        35                  40                  45

Lys Lys Gly Asn Leu Glu Arg Glu Cys Met Glu Glu Ile Cys Ser Tyr
    50                  55                  60

Glu Glu Val Arg Glu Ile Phe Glu Asp Asp Lys Thr Lys Glu Tyr
65                  70                  75                  80

Trp Thr Lys Tyr Lys Asp Gly Asp Gln Cys Glu Ser Ser Pro Cys Gln
                85                  90                  95

Asn Gln Gly Ala Cys Arg Asp Gly Ile Gly Gly Tyr Thr Cys Thr Cys
            100                 105                 110

Ser Glu Gly Phe Glu Gly Lys Asn Cys Glu Leu Phe Val Arg Lys Leu
        115                 120                 125

Cys Arg Leu Asp Asn Gly Asp Cys Asp Gln Phe Cys Arg Glu Glu Gln
    130                 135                 140
```

Asn Ser Val Val Cys Ser Cys Ala Ser Gly Tyr Phe Leu Gly Asn Asp
145                 150                 155                 160

Gly Lys Ser Cys Ile Ser Thr Ala Pro Phe Pro Cys Gly Lys Ile Thr
                165                 170                 175

Thr Gly Arg Arg Lys Arg Ser Val Ala Leu Asn Thr Ser Asp Ser Glu
            180                 185                 190

Leu Asp Leu Glu Asp Ala Leu Leu Asp Glu Asp Phe Leu Ser Pro Thr
        195                 200                 205

Glu Asn Pro Ile Glu Leu Leu Asn Leu Asn Glu Thr Gln Pro Glu Arg
    210                 215                 220

Ser Ser Asp Asp Leu Val Arg Ile Val Gly Gly Arg Glu Cys Lys Asp
225                 230                 235                 240

Gly Glu Cys Pro Trp Gln Ala Leu Leu Ile Asn Glu Asp Asn Glu Gly
                245                 250                 255

Phe Cys Gly Gly Thr Ile Leu Asn Glu Phe Tyr Ile Leu Thr Ala Ala
                260                 265                 270

His Cys Leu His Gln Ala Arg Arg Phe Lys Val Arg Val Gly Asp Arg
            275                 280                 285

Asn Thr Glu Lys Glu Glu Gly Asn Glu Met Val His Glu Val Asp Val
        290                 295                 300

Val Ile Lys His Asn Lys Phe Gln Arg Asp Thr Tyr Asp Tyr Asp Ile
305                 310                 315                 320

Ala Val Leu Arg Leu Lys Thr Pro Ile Thr Phe Arg Met Asn Val Ala
                325                 330                 335

Pro Ala Cys Leu Pro Gln Lys Asp Trp Ala Glu Ser Thr Leu Met Thr
                340                 345                 350

Gln Lys Thr Gly Ile Val Ser Gly Phe Gly Arg Thr His Glu Lys Gly
            355                 360                 365

Arg Gln Ser Asn Ile Leu Lys Met Leu Glu Val Pro Tyr Val Asp Arg
        370                 375                 380

Asn Thr Cys Lys Leu Ser Thr Ser Phe Ser Ile Thr Gln Asn Met Phe
385                 390                 395                 400

Cys Ala Gly Tyr Glu Ala Lys Leu Glu Asp Ala Cys Gln Gly Asp Ser
                405                 410                 415

Gly Gly Pro His Val Thr Arg Phe Lys Asn Thr Tyr Tyr Val Thr Gly
            420                 425                 430

Ile Val Ser Trp Gly Glu Gly Cys Ala Arg Lys Gly Lys Tyr Gly Ile
        435                 440                 445

Tyr Thr Lys Val Thr Thr Phe Leu Lys Trp Ile Asp Arg Ser Met Lys
    450                 455                 460

Ala Arg Val Gly Pro Thr Ala Glu Thr Pro Arg Thr Ala Gly Pro Pro
465                 470                 475                 480

Asn

<210> SEQ ID NO 4
<211> LENGTH: 481
<212> TYPE: PRT
<213> ORGANISM: Mus musculus

<400> SEQUENCE: 4

Met Gly Ser Pro Val Gln Leu Ser Leu Leu Cys Val Val Leu Ala Ser
1               5                   10                  15

Leu Leu Leu Pro Gly Lys Gly Val Phe Ile Asn Arg Glu Arg Ala Asn
                20                  25                  30

```
Asn Val Leu Ala Arg Thr Arg Arg Ala Asn Ser Phe Glu Glu Phe
        35                  40                  45

Lys Lys Gly Asn Leu Glu Arg Glu Cys Met Glu Glu Ile Cys Ser Tyr
 50                  55                  60

Glu Glu Val Arg Glu Ile Phe Glu Asp Glu Lys Thr Lys Glu Tyr
 65                  70                  75                  80

Trp Thr Lys Tyr Lys Asp Gly Asp Gln Cys Glu Ser Ser Pro Cys Gln
                 85                  90                  95

Asn Gln Gly Ala Cys Arg Asp Gly Ile Gly Gly Tyr Thr Cys Thr Cys
                100                 105                 110

Ser Glu Gly Phe Glu Gly Lys Asn Cys Glu Leu Phe Val Arg Lys Leu
            115                 120                 125

Cys Arg Leu Asp Asn Gly Asp Cys Asp Gln Phe Cys Arg Glu Glu Gln
        130                 135                 140

Asn Ser Val Val Cys Ser Cys Ala Ser Gly Tyr Phe Leu Gly Asn Asp
145                 150                 155                 160

Gly Lys Ser Cys Ile Ser Thr Ala Pro Phe Pro Cys Gly Lys Ile Thr
                165                 170                 175

Thr Gly Arg Arg Lys Arg Ser Val Ala Leu Asn Thr Ser Asp Ser Glu
            180                 185                 190

Leu Asp Leu Glu Asp Ala Leu Leu Asp Glu Asp Phe Leu Ser Pro Thr
        195                 200                 205

Glu Asn Pro Ile Glu Leu Leu Asn Leu Asn Glu Thr Gln Pro Glu Arg
    210                 215                 220

Ser Ser Asp Asp Leu Val Arg Ile Val Gly Gly Arg Glu Cys Lys Asp
225                 230                 235                 240

Gly Glu Cys Pro Trp Gln Ala Leu Leu Ile Asn Glu Asp Asn Glu Gly
                245                 250                 255

Phe Cys Gly Gly Thr Ile Leu Asn Glu Phe Tyr Ile Leu Thr Ala Ala
            260                 265                 270

His Cys Leu His Gln Ala Arg Arg Phe Lys Val Arg Val Gly Asp Arg
        275                 280                 285

Asn Thr Glu Lys Glu Glu Gly Asn Glu Met Val His Glu Val Asp Val
    290                 295                 300

Val Ile Lys His Asn Lys Phe Gln Arg Asp Thr Tyr Asp Tyr Asp Ile
305                 310                 315                 320

Ala Val Leu Arg Leu Lys Thr Pro Ile Thr Phe Arg Met Asn Val Ala
                325                 330                 335

Pro Ala Cys Leu Pro Gln Lys Asp Trp Ala Glu Ser Thr Leu Met Thr
            340                 345                 350

Gln Lys Thr Gly Ile Val Ser Gly Phe Gly Arg Thr His Glu Lys Gly
        355                 360                 365

Arg Gln Ser Asn Ile Leu Lys Met Leu Glu Val Pro Tyr Val Asp Arg
    370                 375                 380

Asn Thr Cys Lys Leu Ser Thr Ser Phe Ser Ile Thr Gln Asn Met Phe
385                 390                 395                 400

Cys Ala Gly Tyr Glu Ala Lys Leu Glu Asp Ala Cys Gln Gly Asp Ser
                405                 410                 415

Gly Gly Pro His Val Thr Arg Phe Lys Asn Thr Tyr Tyr Val Thr Gly
            420                 425                 430

Ile Val Ser Trp Gly Glu Gly Cys Ala Arg Lys Gly Lys Tyr Gly Ile
        435                 440                 445
```

```
Tyr Thr Lys Val Thr Thr Phe Leu Lys Trp Ile Asp Arg Ser Met Lys
    450             455             460

Ala Arg Val Gly Pro Thr Ala Glu Thr Pro Arg Thr Ala Gly Pro Pro
465             470             475             480

Asn
```